United States Patent
Li et al.

(10) Patent No.: US 9,957,393 B2
(45) Date of Patent: *May 1, 2018

(54) MONOAZO DYES WITH CYCLIC AMINE AS FLUORESCENCE QUENCHERS

(71) Applicant: Enzo Biochem, Inc., New York, NY (US)

(72) Inventors: Zaiguo Li, Little Neck, NY (US); Praveen Pande, Holbrook, NY (US); Natarajan Raju, Kendall Park, NY (US)

(73) Assignee: Enzo Biochem, Inc., New York, NY (US)

( * ) Notice: Subject to any disclaimer, the term of this patent is extended or adjusted under 35 U.S.C. 154(b) by 444 days.

This patent is subject to a terminal disclaimer.

(21) Appl. No.: 14/672,944

(22) Filed: Mar. 30, 2015

(65) Prior Publication Data

US 2016/0289779 A1 Oct. 6, 2016

(51) Int. Cl.
   C09B 29/44 (2006.01)
   C09B 56/00 (2006.01)
   C12Q 1/68 (2018.01)
   C12Q 1/70 (2006.01)

(52) U.S. Cl.
   CPC ........ *C09B 29/3643* (2013.01); *C09B 56/005* (2013.01); *C12Q 1/68* (2013.01); *C12Q 1/6818* (2013.01); *C12Q 1/6846* (2013.01); *C12Q 1/6876* (2013.01); *C12Q 1/708* (2013.01); *C12Q 2565/101* (2013.01)

(58) Field of Classification Search
   CPC ................................................. C09B 29/3643
   USPC ........................................ 534/798; 536/26.6
   See application file for complete search history.

(56) References Cited

U.S. PATENT DOCUMENTS

| | | |
|---|---|---|
| 4,868,103 A | 9/1989 | Stavrianopoulos et al. |
| 5,118,801 A | 6/1992 | Lizardi et al. |
| 5,210,015 A | 5/1993 | Gelfand et al. |
| 5,401,847 A | 3/1995 | Glazer et al. |
| 5,455,175 A | 10/1995 | Wittwer et al. |
| 5,538,848 A | 7/1996 | Livak et al. |
| 5,580,990 A | 12/1996 | Van Den Berg et al. |
| 5,646,264 A | 7/1997 | Glazer et al. |
| 5,800,996 A | 9/1998 | Lee et al. |
| 5,866,636 A | 2/1999 | Nitto et al. |
| 5,919,630 A | 7/1999 | Nadeau et al. |
| 5,925,517 A | 7/1999 | Tyagi et al. |
| 5,994,056 A | 11/1999 | Higuchi et al. |
| 6,008,373 A | 12/1999 | Waggoner et al. |
| 6,080,868 A | 6/2000 | Lee et al. |
| 6,150,097 A | 11/2000 | Tyagi et al. |
| 6,174,670 B1 | 1/2001 | Wittwer et al. |
| 6,323,337 B1 | 11/2001 | Singer et al. |
| 6,348,596 B1 | 2/2002 | Lee et al. |
| 6,593,465 B1 | 7/2003 | Wolff et al. |
| 6,790,945 B2 * | 9/2004 | Lukhtanov ............ C07C 245/08 435/6.1 |
| 7,019,129 B1 | 3/2006 | Cook et al. |
| 7,109,312 B2 | 9/2006 | Cook et al. |
| 7,439,341 B2 | 10/2008 | Laikhter et al. |
| 7,476,735 B2 | 1/2009 | Laikhter et al. |
| 7,504,495 B2 | 3/2009 | Lomholt et al. |
| 7,582,432 B2 | 9/2009 | Cook et al. |
| 7,879,986 B2 | 2/2011 | Berry et al. |
| 7,956,169 B1 | 6/2011 | Laikhter et al. |
| 8,241,179 B2 | 8/2012 | Shin et al. |
| 8,410,255 B2 | 4/2013 | Cook et al. |
| 8,440,399 B2 | 5/2013 | Cook et al. |
| 2003/0225247 A1 | 12/2003 | Stavrianopoulos et al. |
| 2005/0137388 A1 | 6/2005 | Rabbani et al. |
| 2010/0311184 A1 | 12/2010 | Diwu et al. |
| 2014/0213471 A1 | 7/2014 | Rajagopal et al. |

FOREIGN PATENT DOCUMENTS

| | | |
|---|---|---|
| DE | 102005050833 | 4/2007 |
| DE | 102005050834 | 4/2007 |
| EP | 0040780 | 5/1981 |
| EP | 0070685 | 1/1983 |
| EP | 0102729 | 3/1984 |
| EP | 2078045 | 5/2008 |
| EP | 2397464 | 12/2011 |
| EP | 2868702 | 5/2015 |
| JP | S5986658 | 10/1982 |
| JP | S5930861 | 2/1984 |
| JP | S60221464 | 6/1984 |
| WO | WO1995/13399 | 5/1995 |
| WO | WO1996/30214 | 10/1996 |

(Continued)

OTHER PUBLICATIONS

Arya et al., "Basic principles of real-time quantitative PCR," *Expert Rev. Mol. Diagn.*, vol. 5, No. 2, pp. 209-219 (2005).
Gibson et al., "A Novel Method for Real Time Quantitative RT-PCR," *Genome Research*, vol. 6, pp. 995-1001 (1996).
Gill et al., "Nucleic Acid isothermal Amplification Technologies—A Review," *Nucleosides, Nucleotides, and Nucleic Acids*, vol. 27, pp. 224-243 (2008).
Gullberg et al., "Cytokine detection by antibody-based proximity ligation," *PNAS*, vol. 101, No. 22, pp. 8420-8424.
Livak et al., "Oligonucleotides with Fluorescent Dyes at Opposite Ends Provide a Quenched Probe System Useful for Detecting PCR Product and Nucleic Acid Hybridization," *PCR Methods and Applications*, vol. 4, pp. 357-362 (1995).
Marras et al., "Real-time assays with molecular beacons and other fluorescent nucleic acid hybridization probes," *Clinica Chimica Acta*, vol. 363, pp. 48-60 (2006).
Niemeyer et al., "Immuno-PCR: high sensitivity detection of proteins by nucleic acid amplification," *TRENDS in Biotechnology*, vol. 23, No. 4, 9 pages.
Wittwer et al., "Continuous Fluorescence Monitoring of Rapid Cycle DNA Amplification," *BioTechniques*, vol. 22, No. 1, pp. 130-138 (1997).
Wong et al., "Real-time PCR for mRNA quantitation," *BioTechniques*, vol. 39, No. 1, pp. 75-85 (2005).

(Continued)

Primary Examiner — Jezia Riley
(74) Attorney, Agent, or Firm — Paul Diamond, Esq.

(57) ABSTRACT

The present disclosure provides reactive quencher dyes that can be used in the detection and/or quantification of desirable target molecules, such as proteins, nucleic acids and various cellular organelles. These dyes are essentially non-fluorescent but are efficient quenchers of various fluorescent dyes. Also, provided are methods of using the dyes, bioprobes incorporating dyes and methods of using the bioprobes. The quencher dyes described herein are modified to provide beneficial properties.

3 Claims, 11 Drawing Sheets

(56) References Cited

FOREIGN PATENT DOCUMENTS

Figure 1:
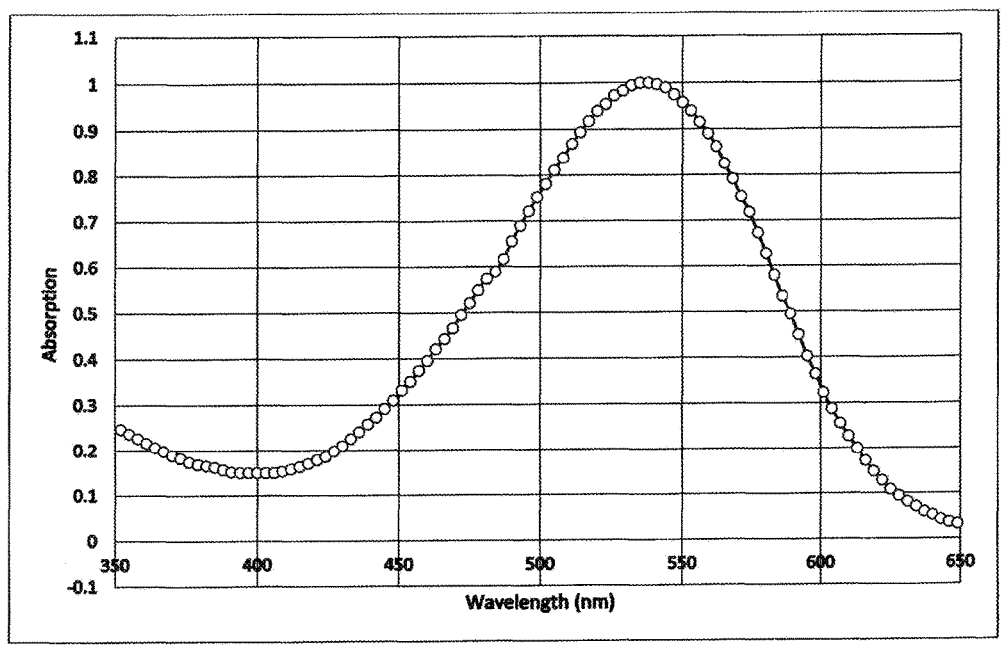

| WO | WO1999/28500 | 6/1999 |
|---|---|---|
| WO | WO1999/29905 | 6/1999 |
| WO | WO1999/49293 | 9/1999 |
| WO | WO1999/63112 | 12/1999 |
| WO | WO2001/86001 | 11/2001 |
| WO | WO2006/132588 | 12/2006 |
| WO | WO2014/021680 | 2/2014 |

OTHER PUBLICATIONS

Chevalier, Arnaud et al., Bioconjugatable Azo-Based Dark-Quencher Dyes: Synthesis and Application to Protease-Activatable Far-Red Fluorescent Probes, *Chem. Eur. J.*, vol. 19, pp. 1686-1699 (2013).

Crisalli, Pete et al., "Multiple Pathway Quenchers: Efficient Quenching of Common Fluorophores," *Bioconjug Chem.*, vol. 22, No. 11, pp. 2345-2354 (2011).

Pauff, Steven et al., "A Trifluoroacetic Acid-labile Sulfonate Protecting Group and Its Use in the Synthesis of a Near-IR Fluorophore," *The Journal of Organic Chemistry*, vol. 78, pp. 711-716 (2013).

Pauff, Steven et al., "Synthesis of Naer-IR Fluorescent Oxazine Dyes with Esterase-Labile Sulfonate Esters," *Organic Letters*, vol. 13, No. 23, pp. 6196-6199 (2011).

Wang, Qunzhao et al., "Multicolor Monitoring of Dysregulated Protein Kinases in Chronic Myelogencus Leukemia," *ACS Chemical biology*, vol. 5, No. 9, pp. 887-895 (2010).

International Preliminary Report on Patentability for PCT/US2015/047363 filed Aug. 28, 2015 dated Oct. 12, 2017.

Bauman, Proceedings of SPIE—The International Society for Optical Engineering, 4517, Lightmetry: Metrology, Spectroscopy, and Testing Techniques Using Light, pp. 222-225, abstract (2001).

\* cited by examiner

The spectrum was recorded in methanol, $\lambda_{max}$ = 535 nm.

The spectrum was recorded in methanol, $\lambda_{max}$ = 517 nm.

The spectrum was recorded in methanol, $\lambda_{max}$ = 389 nm.

The spectrum was recorded in methanol, $\lambda_{max}$ = 561 nm.

The spectrum was recorded in methanol, $\lambda_{max}$ = 611 nm.

The spectrum was recorded in methanol, $\lambda_{max}$ = 583 nm.

MONOAZO DYES WITH CYCLIC AMINE AS FLUORESCENCE QUENCHERS

SEQUENCE LISTING

The instant application contains a Sequence Listing which has been submitted electronically in ASCII format and is hereby incorporated by reference in its entirety. Said ASCII copy, created on Feb. 2, 2018, is named ENZ-111-SL_ST25.txt and is 817 bytes in size.

1. BACKGROUND

Current methods for detecting and/or quantifying nucleic acids of interest in clinical samples include nucleic acid amplification and real-time detection. See. e.g., U.S. Pat. Nos. 5,994,056 and 6,174,670 (measuring enhanced fluorescence of intercalating agents bound to double-stranded nucleic acids); and U.S. Pat. Nos. 5,455,175 and 6,174,670 (real time measurements carried out during the course of the reaction using a PCR cycler machine equipped with a fluorescence detection system and capillary tubes for the reactions). In these methods, as the amount of double-stranded material increases during amplification, the amount of signal also increases. Accordingly, the sensitivity of these systems depends upon a sufficient amount of double-stranded nucleic acid being produced to generate a signal that is distinguishable from background fluorescence. A variation of this system uses PCR primers modified with quenchers that reduce signal generation of fluorescent intercalators bound to a primer dimer molecule. See, e.g., U.S. Pat. No. 6,323,337.

Another method of detecting and/or quantifying nucleic acids of interest includes incorporation of fluorescent labels. See, e.g., U.S. Pat. No. 5,866,336. In this system, signal generation is dependent upon the incorporation of primers into double-stranded amplification products. The primers are designed such that they have extra sequences added onto their 5' ends. In the absence of a complementary target molecule, the primers adopt stem-loop structures through intramolecular hybridization that bring a fluorescence resonance energy transfer (FRET) quencher into proximity with an energy donor, thereby preventing fluorescence. However, when a primer becomes incorporated into double-stranded amplicons, the quencher and donor are physically separated and the donor produces a fluorescent signal. The specificity of this system depends upon the specificity of the amplification reaction itself. Since the stem-loop sequences are derived from extra sequences, the $T_m$ profile of signal generation is the same whether the amplicons were derived from the appropriate target molecules or from non-target sequences.

In addition to incorporation-based assays, probe-based systems can also be used for real-time analysis. For instance, a dual probe system can be used in a homogeneous assay to detect the presence of appropriate target sequences. In this method, one probe comprises an energy donor and the other probe comprises an energy acceptor. See European patent application publication no. 0 070 685. Thus, when the target sequence is present, the two probes can bind to adjacent sequences and energy transfer will take place. In the absence of target sequences, the probes remain unbound and no energy transfer takes place. Even if by chance there are non-target sequences in a sample that are sufficiently homologous that binding of one or both probes takes place, no signal is generated since energy transfer requires that both probes bind in a particular proximity to each other. See U.S. Pat. No. 6,174,670. The primer annealing step during each individual cycle can also allow the simultaneous binding of each probe to target sequences providing an assessment of the presence and amount of the target sequences. In a further refinement of this method, one of the primers comprises an energy transfer element and a single energy transfer probe is used. Labeled probes have also been used in conjunction with fluorescent intercalators, which combines the specificity of the probe methodology with the enhancement of fluorescence derived from binding to nucleic acids. See e.g., U.S. Pat. No. 4,868,103 and PCT Publication no. WO 99/28500.

Other types of probes used in real-time detection and/or quantification of nucleic acids of interest include an energy donor and an energy acceptor in the same nucleic acid. In assays employing these probes, the energy acceptor "quenches" fluorescent energy emission in the absence of complementary targets. See, e.g., U.S. Pat. No. 5,118,801 ("molecular beacons" used where the energy donor and the quencher are kept in proximity by secondary structures formed by internal base pairing). When target sequences are present, complementary sequences in the molecular beacons linearize by hybridizing to the target, thereby separating the donor and the acceptor such that the acceptor no longer quenches the emission of the donor, which produces signal. In Taqman, use is made of the double-stranded selectivity of the exonuclease activity of Taq polymerase. See U.S. Pat. No. 5,210,015. When target molecules are present, hybridization of the probe to complementary sequences converts the single-stranded probe into a substrate for the exonuclease. Degradation of the probe separates an energy transfer donor from the quencher, thereby releasing light from the donor. See U.S. Patent Publication no. 2005/0137388 (describing various formats for utilization of FRET interactions in various nucleic acid assays).

Probes comprising a non-fluorescent dark dye as energy acceptor (quencher) have also been used in the methods described above. When in close proximity, quenchers absorb emitted fluorescence from a donor dye and give no emission. Dabcyl is one such quencher with many applications, but its short absorption wavelength limits its use only to fluorescent reporters with short emission wavelengths, such as fluorescein and coumarin dyes. See, e.g., U.S. Pat. Nos. 5,866,336, 5,919,630, 5,925,517, and 6,150,097 and PCT publication nos. WO9513399A1, WO9929905A2, WO9949293A2, WO9963112A2. Dark quenchers that are suitable for pairing with long wavelength (red) fluorescent dyes have also been developed, but they generally have more complex structures, such as bisazo dyes (U.S. Pat. Nos. 7,019,129; 7,109,312; 7,582,432; 7,879,986; 8,410,255 and 8,440,399; and PCT publication no. WO2014021680), azo dyes containing nitro-substituted naphthalene moiety (U.S. Pat. Nos. 7,439,341 and 7,476,735), azo dyes containing 1,3,3-trimethyl-2-methyleneindoline ring system (U.S. Pat. No. 7,956,169), nitro-substituted non-fluorescent asymmetric cyanine dyes (U.S. Pat. Nos. 6,080,868 and 6,348,596), N-aryl substituted xanthene dyes (U.S. Pat. No. 6,323,337), dyes containing anthraquinone moieties (U.S. Pat. No. 7,504,495), and azo dyes containing heterocyclic moieties (US publication nos. 2010/0311184, and DE 102005050833 and DE 102005050834). Accordingly, there is a need for dark quencher dyes that have simple, non-complex structures that are able to absorb and quench fluorescence in a wider wavelength range.

2. SUMMARY

The present disclosure provides a series of fluorescence quenchers that are monoazo dyes comprising cyclic amine groups. The monoazo dyes described herein are essentially non-fluorescent in nature but are efficient quenchers of dyes that emit fluorescence over a larger range of wavelengths as compared to known quenchers. In particular embodiments, the quencher dyes described herein quench fluorescence emission over wavelengths from about 500 nm to about 700 nm. As used herein, the terms "quencher," "dark quencher," and "non-fluorescent dark dye" refer interchangeably to the monoazo dyes described herein that have the ability to suppress emission of fluorescence from a donor dye and that do not emit the absorbed fluorescence.

The present disclosure also provides a composition comprising a molecule attached to a monoazo dye described herein. In some embodiments, the molecule is a nucleic acid. In other embodiments, the molecule is a protein. In some embodiments, the monoazo dye is modified by the addition of a reactive group ($R_x$). In other embodiments, the molecule is modified by the addition of a reactive group.

Also provided are processes for qualitatively or quantitatively detecting the presence of a single stranded or double-stranded nucleic acid of interest in a sample using a dark quencher compound described herein.

The present disclosure additionally provides compositions for detecting various nucleic acid targets by techniques comprising but not limited to quantitative PCR and flow cytometry. In various embodiments, the composition is a kit comprising in packaged combination: (a) one or more monoazo dye compounds described herein or a molecule covalently attached to one or more monoazo dye compounds described herein; and (b) instructions for their use. In certain embodiments, the monoazo dye is modified by the addition of a reactive group.

The disclosure further provides a composition comprising a solid support to which is covalently or non-covalently attached one or more of the monoazo dye compounds described herein, wherein the compound or compounds are modified by the addition of a reactive group ($R_x$) for attachment of the dye to a target molecule.

In other embodiments, the monoazo dyes described herein are utilized as a component of one or more probes for use in a multiplex assay for detecting and/or quantifying one or more species of interest in a mixture, such as a biological sample. In a typical multiplex assay two or more distinct species are detected using the a monoazo compound described herein and probes labeled with a donor fluorophore. In these assays preferred species rely on donor-acceptor energy transfer such that the fluorescent species is bright and spectrally well-resolved and the energy transfer between the fluorescent species and the monoazo quencher is efficient.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art or were common general knowledge in the field relevant to the present disclosure as it existed anywhere before the priority date of this application.

The features and advantages of the disclosure will become further apparent from the following detailed description of embodiments thereof.

3. BRIEF DESCRIPTION OF THE FIGURES

Figure 2:
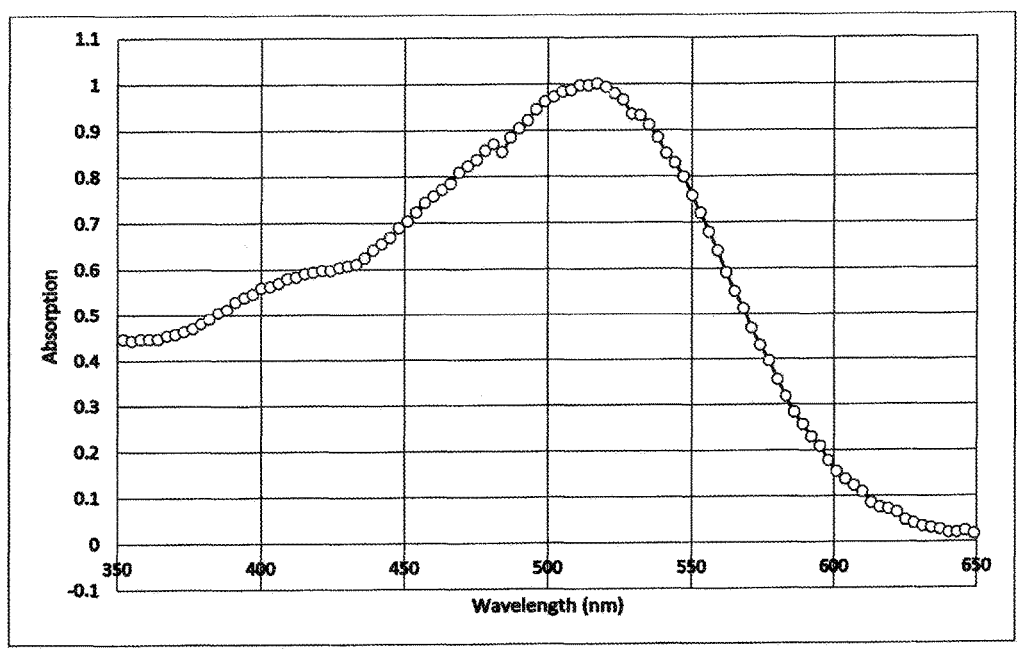
Figure 3:
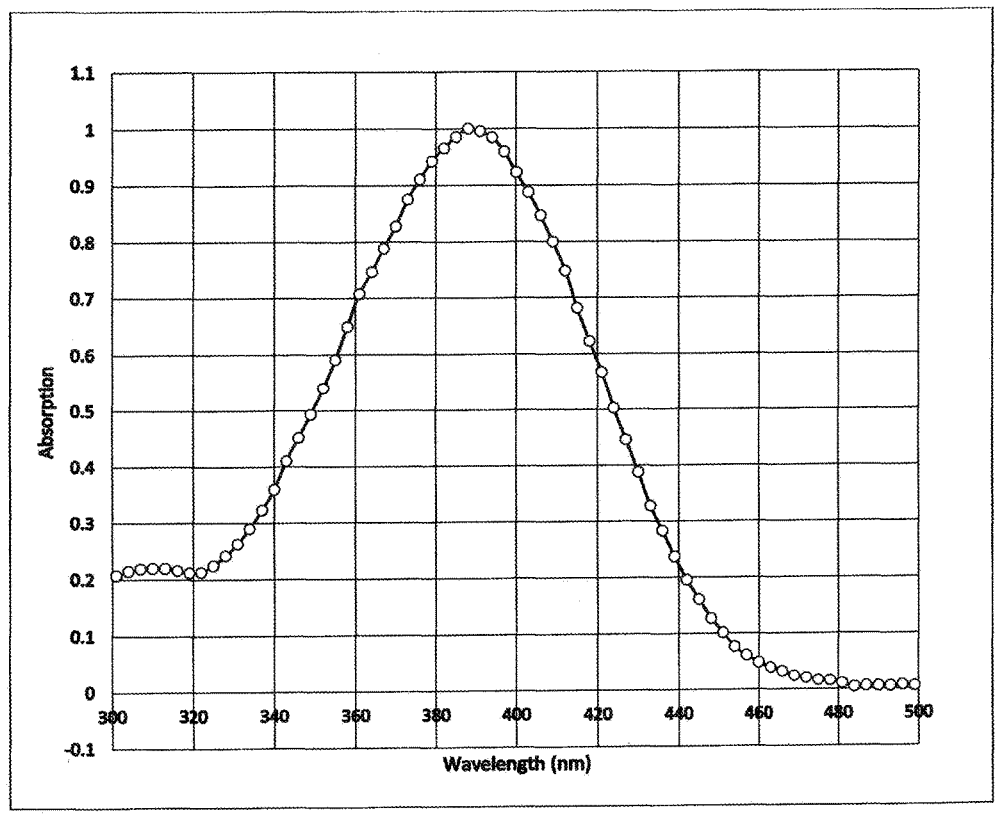
Figure 4:
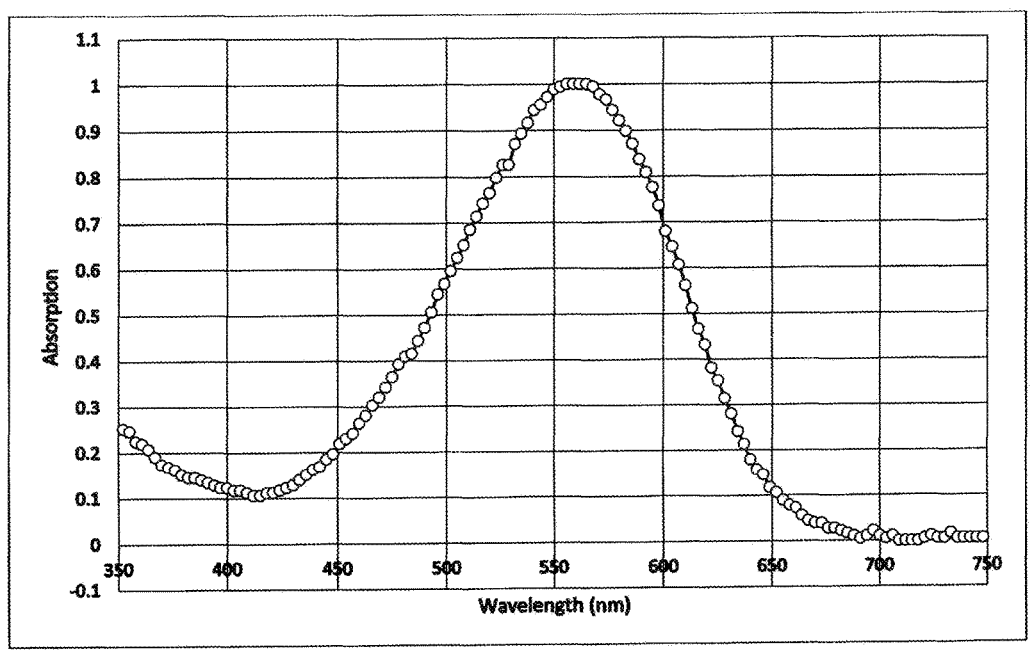
Figure 5:
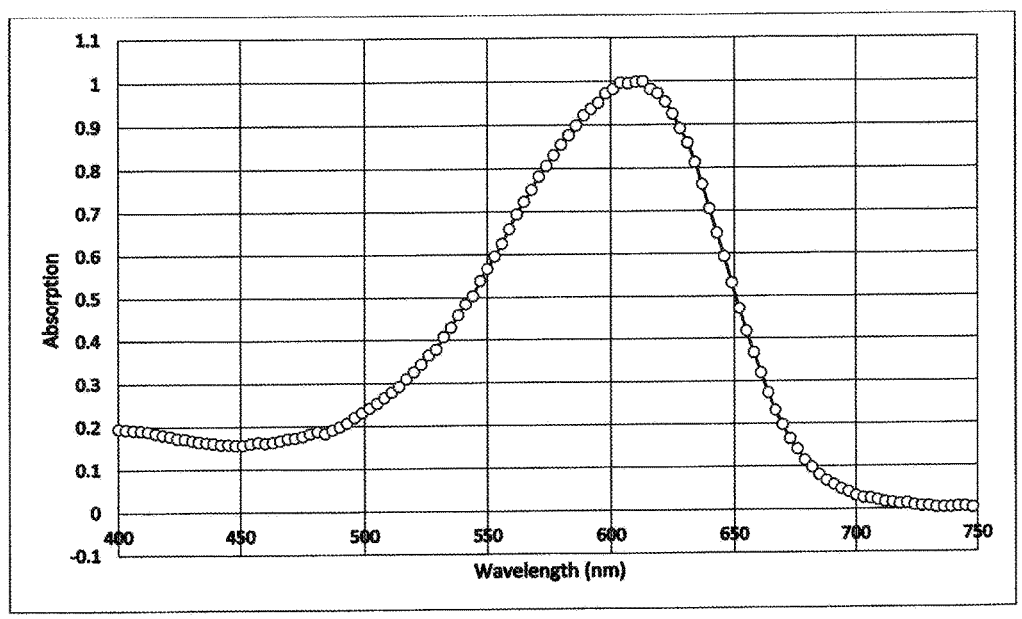
Figure 6:
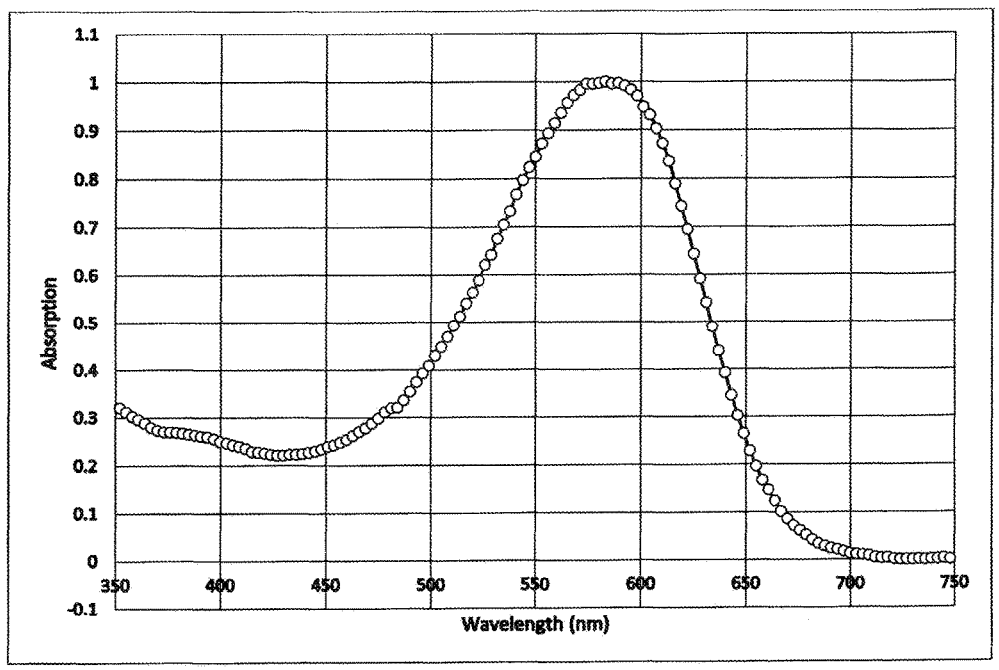
Figure 7:
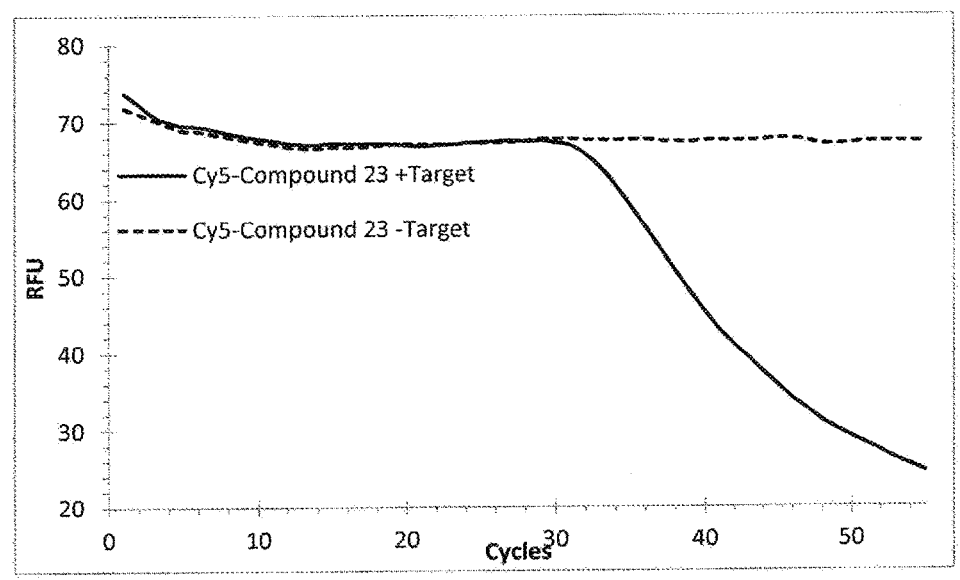
Figure 8:
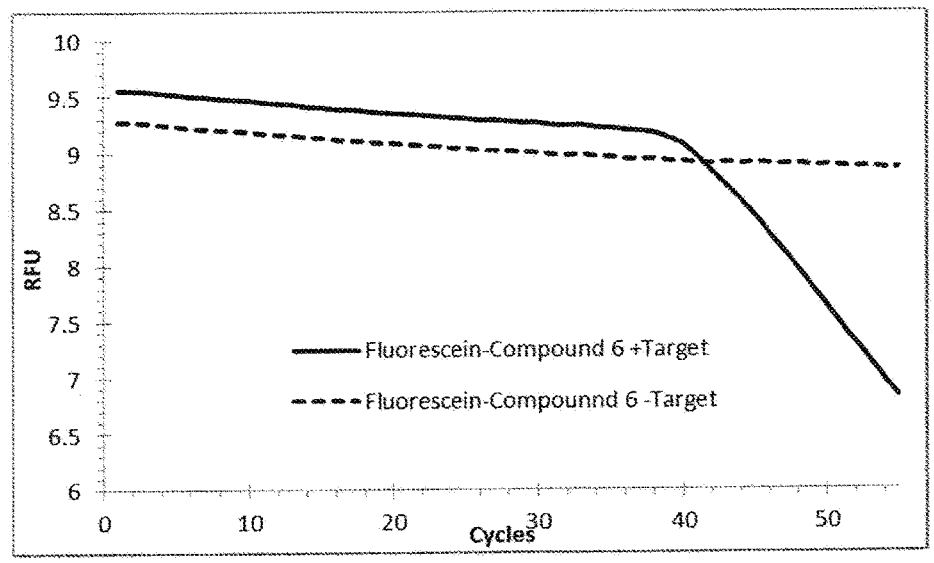
Figure 9:
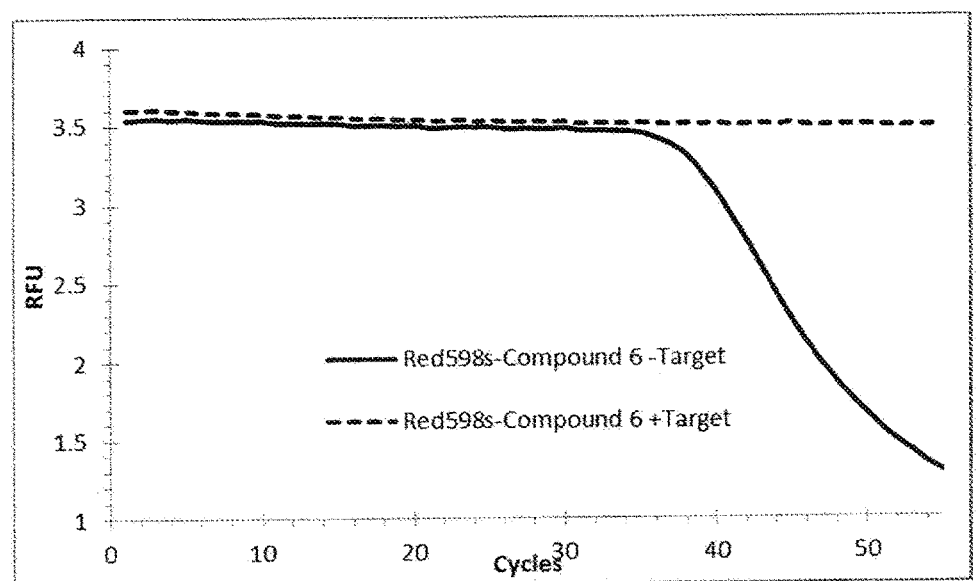
Figure 10:
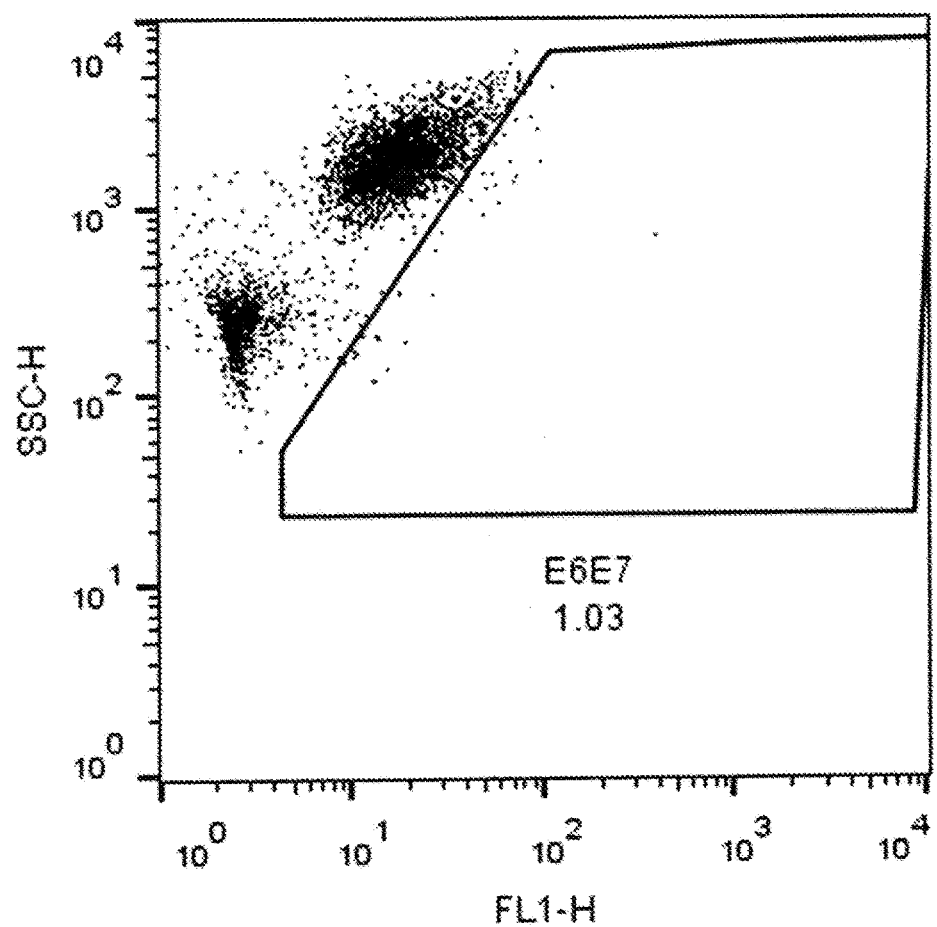
Figure 11:
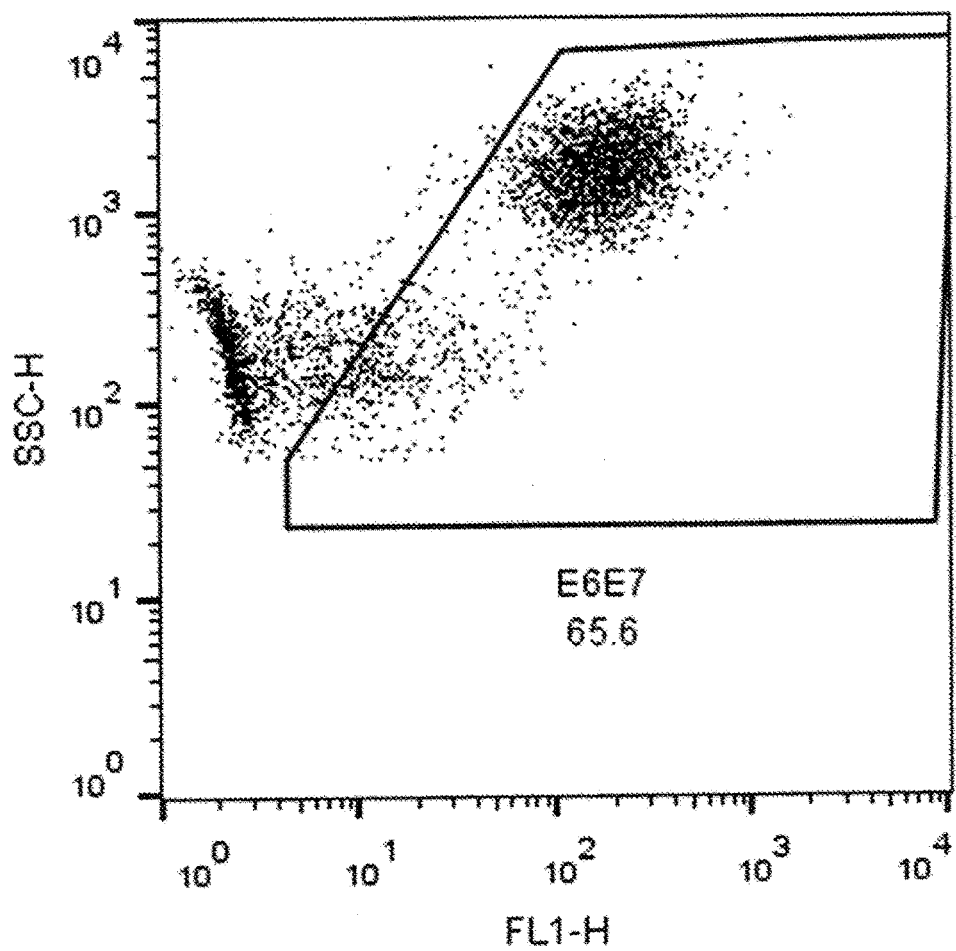

FIG. 1 shows the UV-VIS spectrum of Compound 5.
FIG. 2 shows the UV-VIS spectrum of Compound 8.
FIG. 3 shows the UV-VIS spectrum of Compound 10.
FIG. 4 shows the UV-VIS spectrum of Compound 13.
FIG. 5 shows the UV-VIS spectrum of Compound 15.
FIG. 6 shows the UV-VIS spectrum of Compound 22.
FIG. 7 shows fluorescent trace of amplification (qPCR assay) using Cy5 dye with Compound 23.
FIG. 8 shows fluorescent trace of amplification (qPCR assay) using Fluorescein with Compound 6.
FIG. 9 shows fluorescent trace of amplification (qPCR assay) using Red598s (Enzo Life Sciences, Inc. Farmingdale, N.Y.) with Compound 6.
FIG. 10 shows a Flow Cytometry data of E6/E7 negative Pap smear sample using molecular beacon consisting of Fluorescein and Compound 6.
FIG. 11 shows a Flow Cytometry data of E6/E7 positive Pap smear sample using molecular beacon consisting of Fluorescein and Compound 6.

4. DETAILED DESCRIPTION

In certain embodiments, the disclosure is directed to a monoazo dye having the structure of Formula I:

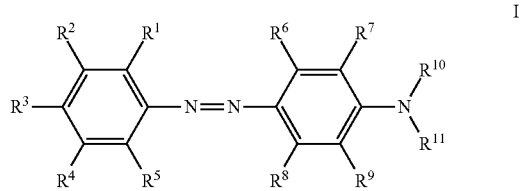

wherein $R^1$, $R^2$, $R^3$, $R^4$, $R^5$, $R^6$, $R^7$, $R^8$, and $R^9$ are each independently selected from H, F, Cl, Br, I, CN, nitro, azido, hydroxyl, amino, hydrazino, aryl, substituted aryl, aroxyl, substituted aroxyl, alkenyl, alkynyl, alkyl, alkoxy, alkylamino, dialkylamino, arylamino, diarylamino, alkyl(aryl)amino, alkanoylamino, alkylthio, alkylcarbonyl, aryl carbonyl, alkylthiocarbonyl, arylthiocarbonyl, alkyloxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, wherein the alkyl or alkoxy groups are saturated or unsaturated, linear or branched, unsubstituted or optionally substituted by F, Cl, Br, I, CN, OH, alkenyl, alkynyl, alkylcarbonyl, amide, thioamide, or Q, and the aryl group is optionally substituted by F, Cl, Br, I, CN, OH, alkenyl, alkynyl, alkylcarbonyl, amide, thioamide, or Q; or one or more of $R^1$ in combination with $R^2$, $R^2$ in combination with $R^3$, $R^3$ in combination with $R^4$, $R^4$ in combination with $R^5$, $R^6$ in combination with $R^7$, and $R^8$ in combination with $R^9$, form a 5- to 10-member ring that is saturated or unsaturated, unsubstituted or optionally substituted with one or more of alkyl, aryl, alkenyl, alkynyl, alkoxy, aroxyl, hydroxyl, F, Cl, Br, I, CN, nitro, alkylsulfonyl, arylsulfonyl, alkylsulfinyl, arylsulfinyl, (thio)carbonyl, (thio)carboxylic acid, (thio)carboxylic acid ester, nitro, amino, (thio)amide, azido, hydrazino, or (thio)phosphonate, wherein the alkyl or alkoxy groups are saturated or unsaturated, linear or branched, substituted or unsubstituted, and the aryl group is optionally substituted with F, Cl, Br, I, CN, OH, alkyl, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

Q is selected from a carboxyl group ($CO_2^-$), a carbonate ester ($COER^{12}$), a sulfonate ester ($SO_2ER^{12}$), a sulfoxide ($SOR^{12}$), a sulfone ($SO_2CR^{12}R^{13}R^{14}$), a sulfonamide ($SO_2NR^{12}R^{13}$), a phosphate ($PO_4^=$), a phosphate monoester ($PO_3^-ER^{12}$), a phosphate diester ($PO_2ER^{12}ER^{13}$), a phosphonate ($PO_3^=$) a phosphonate monoester ($PO_2^-ER^{12}$) a phosphonate diester ($POER^{12}ER^{13}$), a thiophosphate ($PSO_3^=$), a thiophosphate monoester ($PSO_2^-ER^{12}$) a thiophosphate diester ($PSOER^{12}ER^{13}$), a thiophosphonate ($PSO_2^=$), a thiophosphonate monoester ($PSO^-ER^{12}$) a thiophosphonate diester ($PSER^{12}ER^{13}$), a phosphonamide ($PONR^{12}R^{13}NR^{15}R^{16}$), its thioanalogue ($PSNR^{12}R^{13}NR^{15}R^{16}$), a phosphoramide ($PONR^{12}R^{13}NR^{14}NR^{15}R^{16}$), its thioanalogue ($PSNR^{12}R^{13}NR^{14}NR^{15}R^{16}$), a phosphoramidite ($PO_2R^{15}NR^{12}R^{13}$) or its thioanalogue ($POSR^{15}NR^{12}R^{13}$), wherein E is independently O or S;

$R^{10}$ and $R^{11}$ are each independently selected from H, a saturated or unsaturated, linear or branched, unsubstituted or further substituted alkyl group, aryl group, alkylcarbonyl, aryl carbonyl, alkylthiocarbonyl, arylthiocarbonyl, alkoxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, the alkyl or alkoxy portions of which are, alkenyl, alkynyl, alkylcarbonyl, amide, thioamide, or Q, or the aryl portions of which are optionally substituted by F, Cl, Br, I, CN, OH, alkenyl, alkynyl, alkylcarbonyl, amide, thioamide, or Q; or at least one of $R^7$ in combination with $R^{10}$, or $R^9$ in combination with $R^{11}$ forms a 5- to 10-member saturated or unsaturated ring optionally further substituted with one or more saturated or unsaturated, linear or branched, substituted or unsubstituted alkyl, aryl, alkenyl, alkynyl, saturated or unsaturated, linear or branched, substituted or unsubstituted alkoxy, aroxyl, hydroxyl, F, Cl, Br, I, CN, nitro, alkylsulfonyl, arylsulfonyl, alkylsulfinyl, arylsulfinyl, (thio)carbonyl, (thio)carboxylic acid, (thio)carboxylic acid ester, nitro, amino, (thio)amide, azido, hydrazino, or (thio)phosphonate; wherein the aryl group is optionally substituted with one or more of F, Cl, Br, I, CN, OH, alkyl, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

wherein $R^{12}$, $R^{13}$, $R^{14}$, $R^{15}$ and $R^{16}$ are independently selected from hydrogen, a halogen, an amino group, a saturated or unsaturated, linear or branched, substituted or unsubstituted alkyl group, a saturated or unsaturated, branched or linear, substituted or unsubstituted alkoxy group, a substituted or unsubstituted aryl group; or $R^{12}$ in combination with $R^{13}$, $R^{14}$ in combination with $R^{16}$, $R^{12}$ in combination with $R^{14}$, $R^{12}$ in combination with $R^{15}$, $R^{13}$ in combination with $R^{16}$, and $R^{14}$ in combination with $R^{15}$, one or more of which, form a 5- to 10-member ring; and wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ comprises one or more reactive groups Z, selected from isocyanate, isothiocyanate, monochlorotriazine, dichlorotriazine, 4,6-dichloro-1,3,5-triazines, mono- or di-halogen substituted pyridine, mono- or di-halogen substituted diazine, maleimide, haloacetamide, aziridine, sulfonyl halide, carboxylic acid, acid halide, phosphonyl halide, phosphoramidite ($PO_2R^{15}NR^{12}R^{13}$) or its thioanalogue ($POSR^{15}NR^{12}R^{13}$), hydroxysuccinimide ester, hydroxysulfosuccinimide ester, imido ester, azidonitrophenol ester, azide, 3-(2-pyridyl dithio)-propionamide, glyoxal, aldehyde, thiol, amine, hydrazine, hydroxyl, terminal alkene, a terminal alkyne, a platinum coordinate group and an alkylating agent.

In other embodiments, the disclosure is directed to a dye having the structure of Formula II:

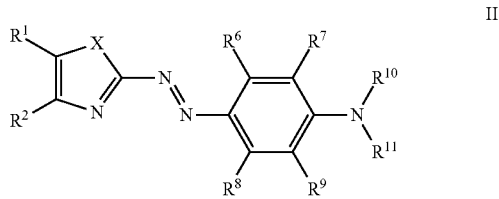

II wherein at least one of $R^1$ or $R^2$ is a nitro group;

X is O, S, or $NR^{17}$, wherein $R^{17}$ is selected from H, an alkyl group that is saturated or unsaturated, linear or branched, unsubstituted, or further substituted by F, Cl, Br, I, CN, OH, alkenyl, alkynyl, alkylcarbonyl, amide, thioamide, or Q, or an aryl group optionally substituted by F, Cl, Br, I, CN, OH, alkenyl, alkynyl, alkylcarbonyl, amide, thioamide, or Q, Q is selected from a carboxyl group ($CO_2^-$), a carbonate ester ($COER^{12}$), a sulfonate ester ($SO_2ER^{12}$), a sulfoxide ($SOR^{12}$), a sulfone ($SO_2CR^{12}R^{13}R^{14}$), a sulfonamide ($SO_2NR^{12}R^{13}$), a phosphate ($PO_4^=$), a phosphate monoester ($PO_3^-ER^{12}$), a phosphate diester ($PO_2ER^{12}ER^{13}$), a phosphonate ($PO_3^=$) a phosphonate monoester ($PO_2^-ER^{12}$) a phosphonate diester ($POER^{12}ER^{13}$), a thiophosphate ($PSO_3^=$), a thiophosphate monoester ($PSO_2^-ER^{12}$) a thiophosphate diester ($PSOER^{12}ER^{13}$), a thiophosphonate ($PSO_2^=$), a thiophosphonate monoester ($PSO^-ER^{12}$) a thiophosphonate diester ($PSER^{12}ER^{13}$), a phosphonamide ($PONR^{12}R^{13}NR^{15}R^{16}$), its thioanalogue ($PSNR^{12}R^{13}NR^{15}R^{16}$), a phosphoramide ($PO_2R^{15}NR^{12}R^{13}$), its thioanalogue ($PSNR^{12}R^{13}NR^{14}NR^{15}R^{16}$), a phosphoramidite ($PO_2R^{15}NR^{12}R^{13}$) or its thioanalogue ($POSR^{15}NR^{12}R^{13}$) and E is independently O or S;

$R^1$, $R^2$, $R^6$, $R^7$, $R^8$, and $R^9$ are each independently selected from H, F, Cl, Br, I, CN, nitro, azido, hydroxyl, amino, hydrazino, aryl, aroxyl, alkenyl, alkynyl, alkyl, alkoxy, alkylamino, dialkylamino, arylamino, diarylamino, alkylamino, alkylarylamino, alkanoylamino, alkylthio, alkylcarbonyl, aryl carbonyl, alkylthiocarbonyl, arylthiocarbonyl, alkyloxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, wherein the alkyl or alkoxy groups are saturated or unsaturated, linear or branched, unsubstituted or further substituted by F, Cl, Br, I, CN, OH, alkenyl, alkynyl, alkylcarbonyl, amide, thioamide, or Q, and the aryl group is optionally substituted by F, Cl, Br, I, CN, OH, alkenyl, alkynyl, alkylcarbonyl, amide, thioamide, or Q;

one or more of $R^1$ in combination with $R^{17}$, $R^6$ in combination with $R^7$, and $R^8$ in combination with $R^9$ form a saturated or unsaturated 5- to 10-member ring optionally substituted by one or more of a saturated or unsaturated, linear or branched, substituted or unsubstituted alky group, aryl, alkenyl, alkynyl, a saturated or unsaturated, branched or linear, substituted or unsubstituted alkoxy group, aroxyl, hydroxyl, F, Cl, Br, I, CN, nitro, alkylsulfonyl, arylsulfonyl, alkylsulfinyl, arylsulfinyl, carbonyl, thiocarbonyl, carboxylic acid, thiocarboxylic acid, carboxylic acid ester, thiocarboxylic acid ester, nitro, amino, amide, thioamide, azido, hydrazino, phosphonate or thiophosphonate, wherein the aryl group is optionally substituted with F, Cl, Br, I, CN, OH, alkyl, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

$R^{10}$ and $R^{11}$ are each independently selected from H, alkyl, aryl, alkylcarbonyl, aryl carbonyl, alkylthiocarbonyl, arylthiocarbonyl, alkoxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, wherein the alkyl group and the alkoxy group are each independently saturated or unsaturated, linear or branched, unsubstituted or further substituted by F, Cl, Br, I, CN, OH, alkenyl, alkynyl, alkylcarbonyl, amide, thioamide, or Q, and the aryl group is unsubstituted or optionally substituted by F, Cl, Br, I, CN, OH, alkenyl, alkynyl, alkylcarbonyl, amide, thioamide, or Q;

$R^{12}$, $R^{13}$, $R^{14}$, $R^{15}$ and $R^{16}$ are each independently selected from hydrogen, a halogen, an amino group, a saturated or unsaturated, linear or branched, substituted or unsubstituted alkyl group, a saturated or unsaturated, linear or branched, substituted or unsubstituted alkoxy group, a substituted or unsubstituted aryl group; or one or more of $R^{12}$ in combination with $R^{13}$, $R^{14}$ in combination with $R^{16}$, $R^{12}$ in combination with $R^{14}$, $R^{12}$ in combination with $R^{15}$, $R^{13}$ in combination with $R^{16}$, and $R^{14}$ in combination with $R^{15}$ form a 5- to 10-member ring;

at least one of $R^7$ in combination with $R^{10}$, or $R^9$ in combination with $R^{11}$ form a saturated or unsaturated 5- to 10-member ring optionally substituted with alkyl, aryl, alkenyl, alkynyl, alkoxy, aroxyl, hydroxyl, F, Cl, Br, I, CN, nitro, alkylsulfonyl, arylsulfonyl, alkylsulfinyl, arylsulfinyl, carbonyl, thiocarbonyl, carboxylic acid, thiocarboxylic acid, carboxylic acid ester, thiocarboxylic acid ester, nitro, amino, amide, thioamide, azido, hydrazino, phosphonate, or thiophosphonate wherein the alky group and the alkoxy group are each independently saturated or unsaturated, linear or branched, substituted or unsubstituted, and wherein the aryl group is unsubstituted or substituted with F, Cl, Br, I, CN, OH, alkyl, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

$R^{12}$, $R^{13}$, $R^{14}$, $R^{15}$ and $R^{16}$ are independently selected from hydrogen, a halogen, an amino group, a saturated or unsaturated, linear or branched, substituted or unsubstituted alkyl group, a saturated or unsaturated, branched or linear, substituted or unsubstituted alkoxy group, or an unsubstituted or substituted aryl group; or one or more of $R^{12}$ in combination with $R^{13}$, $R^{14}$ in combination with $R^{16}$, $R^{12}$ in combination with $R^{14}$, $R^{12}$ in combination with $R^{15}$, $R^{13}$ in combination with $R^{16}$, and $R^{14}$ in combination with $R^{15}$ form a 5- to 10-member ring; and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ comprises one or more reactive groups Z, independently selected from isocyanate, isothiocyanate, monochlorotriazine, dichlorotriazine, 4,6-dichloro-1,3,5-triazines, mono- or di-halogen substituted pyridine, mono- or di-halogen substituted diazine, maleimide, haloacetamide, aziridine, sulfonyl halide, carboxylic acid, acid halide, phosphonyl halide, phosphoramidite ($PO_2R^{15}NR^{12}R^{13}$) or its thioanalogue ($POSR^{15}NR^{12}R^{13}$), hydroxysuccinimide ester, hydroxysulfosuccinimide ester, imido ester, azido, nitrophenol ester, azide, 3-(2-pyridyl dithio)-propionamide, glyoxal, aldehyde, thiol, amine, hydrazine, hydroxyl, terminal alkene, a terminal alkyne, a platinum coordinate group and an alkylating agent.

4.1 Complex Ring Structures

In certain embodiments, certain R groups are joined together to form one or more fused 5- or 6-membered ring structures. In certain embodiments, the complex rings that are formed between R groups may be unsubstituted or may be further substituted with any of the R groups described previously to form complex ring structures. Examples of rings and complex rings containing the amine group include, but are not limited to:

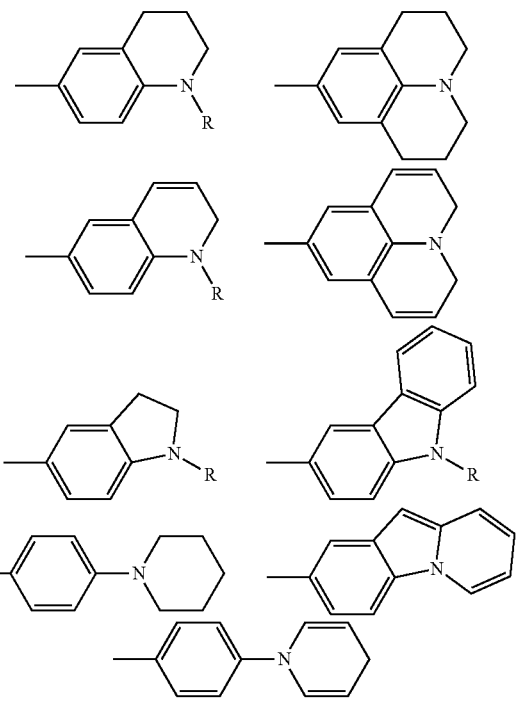

4.2 Reactive Groups and Targets

In other embodiments described herein, at least one of the R groups is a reactive group thereby allowing the dyes to be attached to a target molecule. Examples of reactive groups include, but are not limited to, a nucleophilic reactive group, an electrophilic reactive group, a terminal alkene, a terminal alkyne, a platinum coordinate group or an alkylating agent. The skilled artisan will recognize what types of reactive groups can be used to attach the dark quencher dyes described herein to a particular component in the target molecule.

In certain embodiments, the reactive group is an electrophilic reactive group. Examples of such electrophilic reactive groups include, but not be limited to, isocyanate, isothiocynate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal and aldehyde groups.

In various embodiments, the reactive group is a nucleophilic reactive group. Such nucleophilic reactive groups include, but are not limited to, reactive thiol, amine and hydroxyl groups. During synthesis of dyes, reactive thiol, amine or hydroxyl groups can be protected, and the reactive groups generated after removal of the protective group. In certain embodiments, a dye is attached to a terminal alkene or alkyne group. See, e.g., U.S. Patent Application Serial No. 2003/0225247. In other embodiments, platinum coordinate groups can be used to attach dyes to a target molecule. See U.S. Pat. No. 5,580,990. In yet other embodiments, alkyl groups are used to attach dyes to a target molecule. See U.S. Pat. No. 6,593,465.

Examples of target molecules that can be labeled by the monoazo dyes described herein include, but not be limited to, a nucleoside, a nucleotide, an oligonucleotide, a polynucleotide, a peptide nucleic acid, a protein, a peptide, an enzyme, an antigen, an antibody, a hormone, a hormone receptor, a cellular receptor, a lymphokine, a cytokine, a hapten, a lectin, avidin, strepavidin, digoxygenin, a carbohydrate, an oligosaccharide, a polysaccharide, a lipid, liposomes, a glycolipid, a viral particle, a viral component, a bacterial cell, a bacterial component, a eukaryotic cell, a eukaryotic cell component, a natural drug, a synthetic drug, a glass particle, a glass surface, natural polymers, synthetic polymers, a plastic particle, a plastic surface, a silicaceous particle, a silicaceous surface, an organic molecule, other dyes and derivatives thereof.

In certain embodiments, the nucleoside, nucleotide, oligonucleotide, or polynucleotide comprises one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues, and any combination thereof.

As disclosed above, in certain embodiments, the monoazo dyes described herein can have other dyes as targets, thereby creating composite dyes in which two or more dyes are covalently attached. In various embodiments, the composite dyes have unique properties that are not present in either dye alone. For example, in certain embodiments, if one of the dyes described herein is covalently joined to another dye such that it creates an extended conjugation system, the spectral characteristics of the dye pair may be different than the spectral characteristics of either dye component alone. In other embodiments, the conjugation systems of the joined dyes do not overlap but the proximity allows an internal energy transfer to take place, thereby extending the Stokes shift. See, e.g., U.S. Pat. Nos. 5,401,847; 6,008,373 B1 and 5,800,996. In various embodiments, other properties may also be enhanced by covalently joining two or more dyes. See, e.g., U.S. Patent Application Publication No. 2003/0225247 (two ethidium bromide molecules joined together generates a dye that has enhanced binding to nucleic acids). In certain embodiments, composite dyes exhibit enhanced binding and energy transfer. See, e.g., U.S. Pat. No. 5,646,264. In particular embodiments, composite dyes include not only two dyes, but can comprise oligomeric or polymeric dyes. In certain embodiments, the composite dyes described herein comprise multimers of same dye. In other embodiments, the composite dyes comprise multimers of different dyes. The skilled artisan will appreciate that the identities of the dyes included in multimers are dependent on the desired properties of the dye multimers.

Selected embodiments of the monoazo dyes described herein include, but are not limited to, the illustrated dyes:

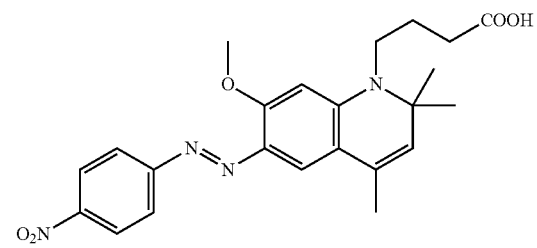

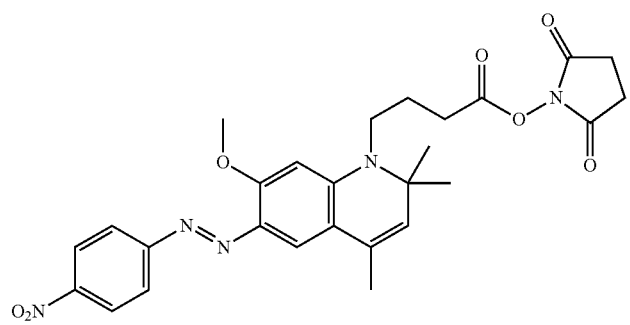

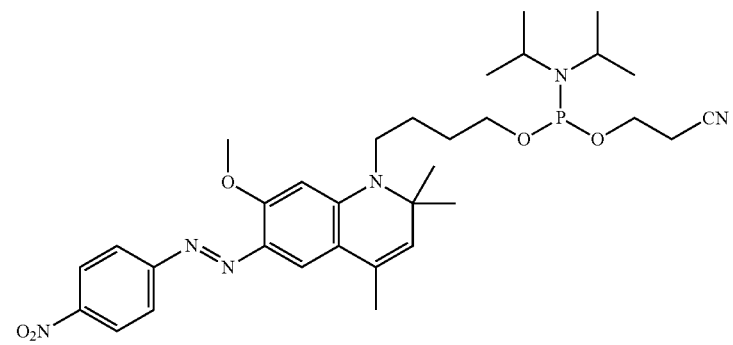

11
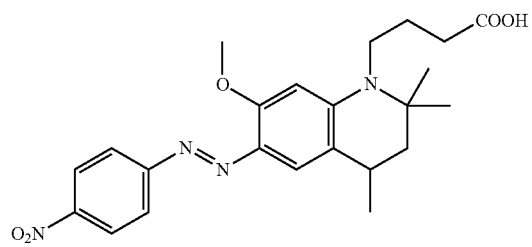
12
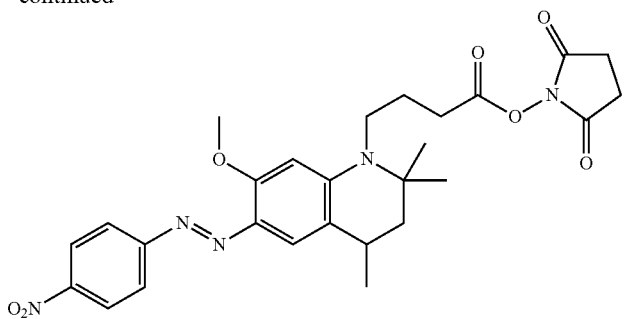
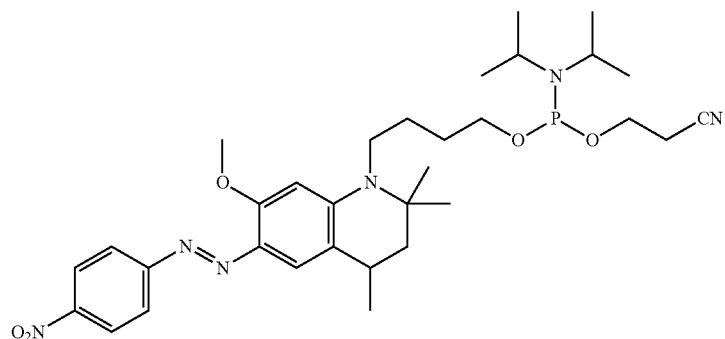
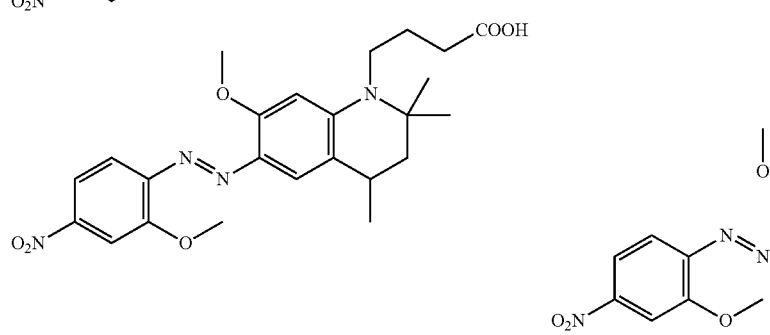
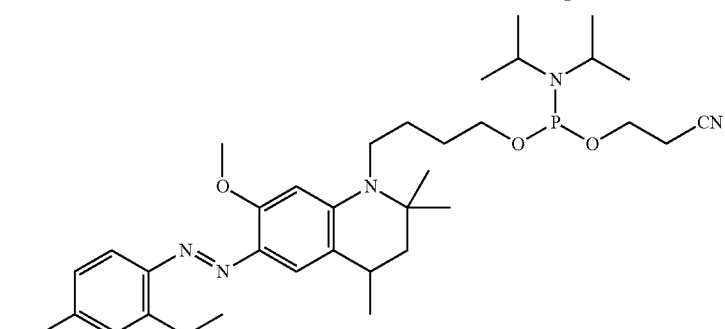
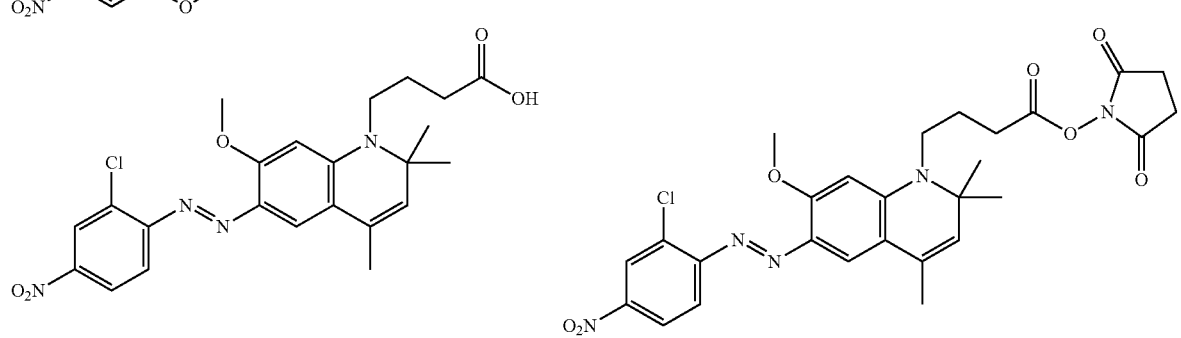

-continued
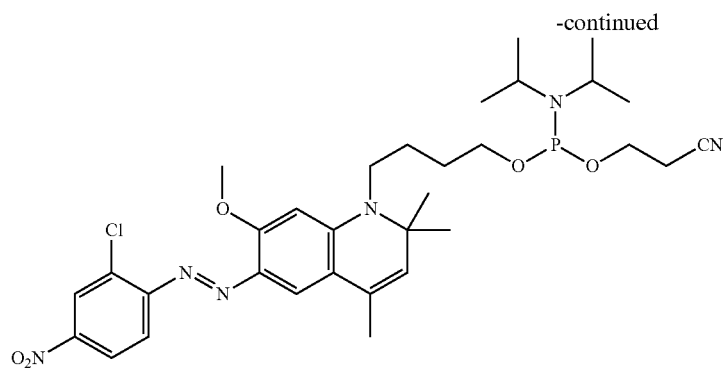
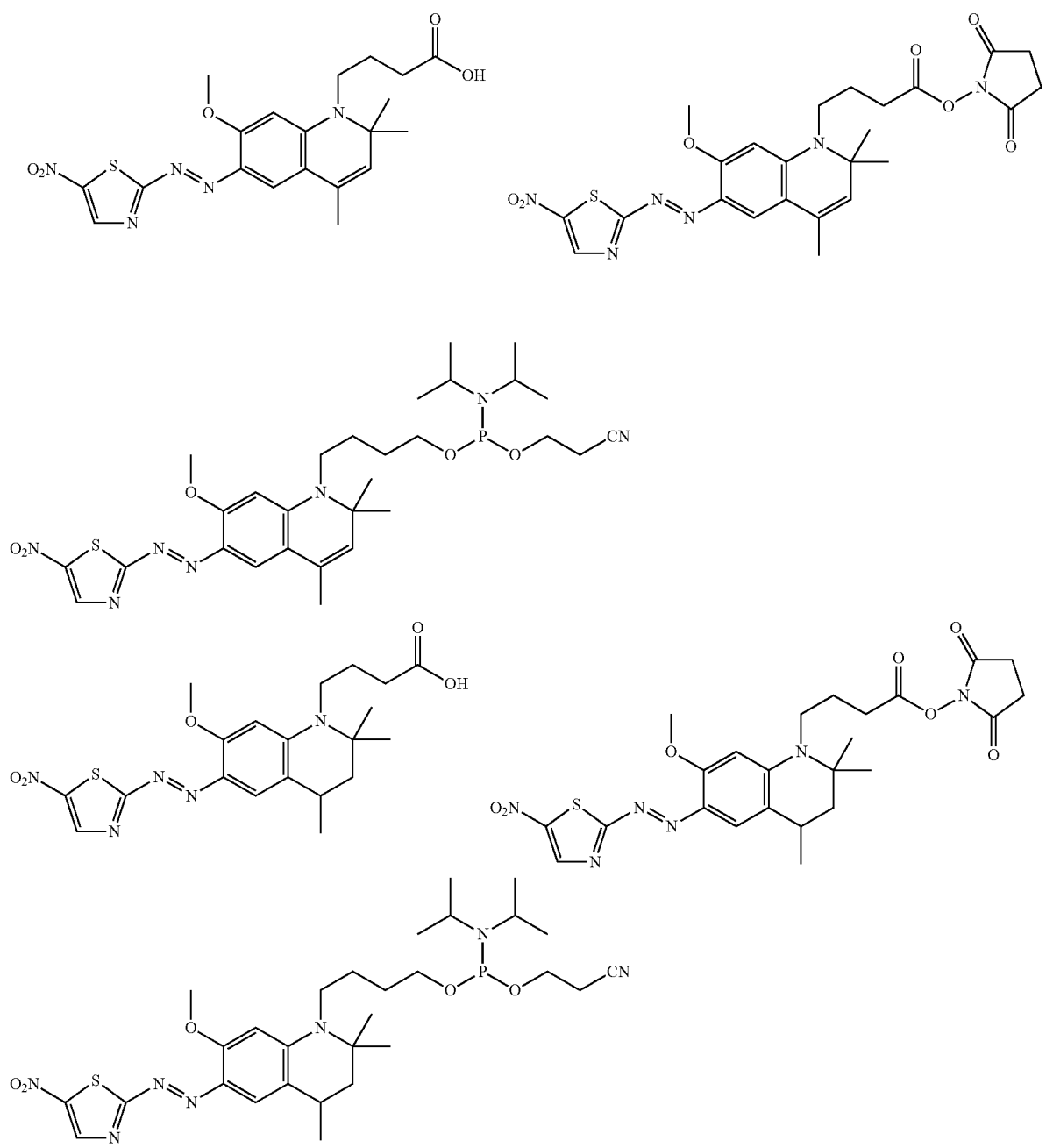

-continued
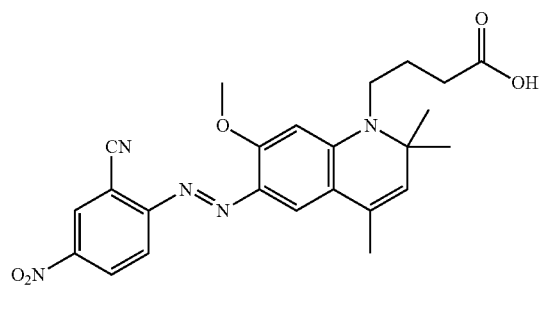
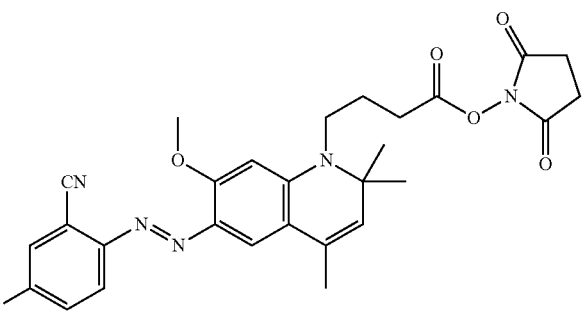
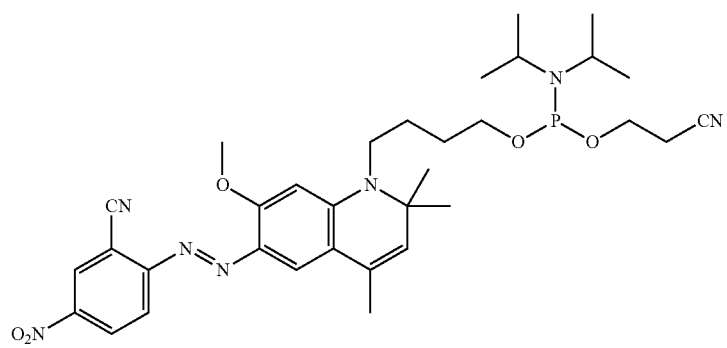
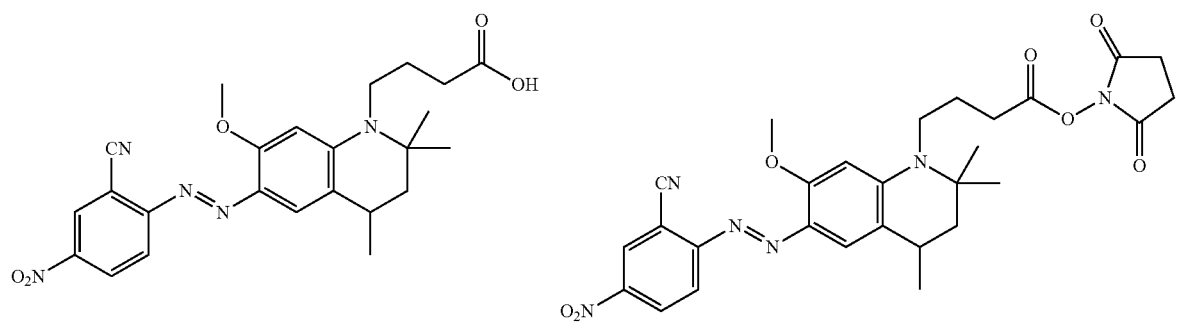
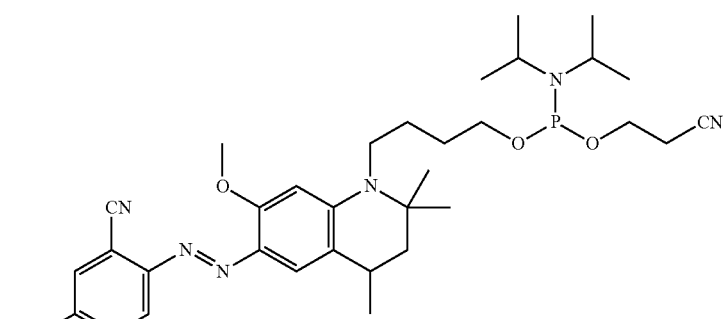
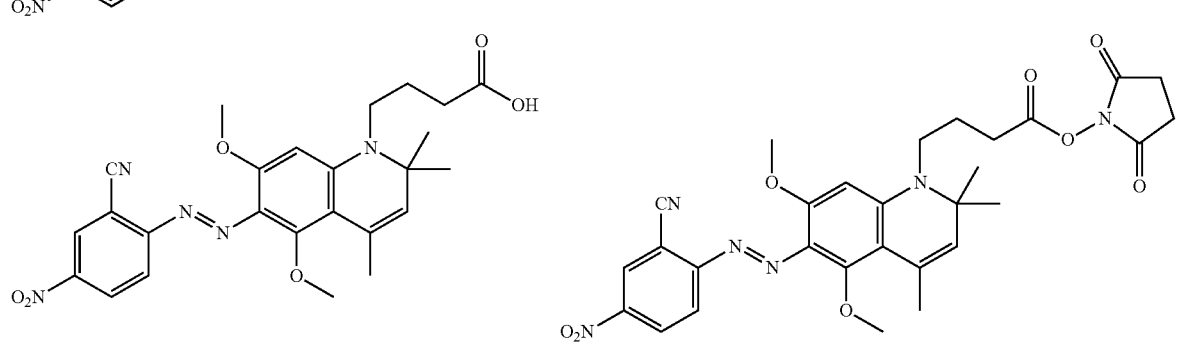

-continued

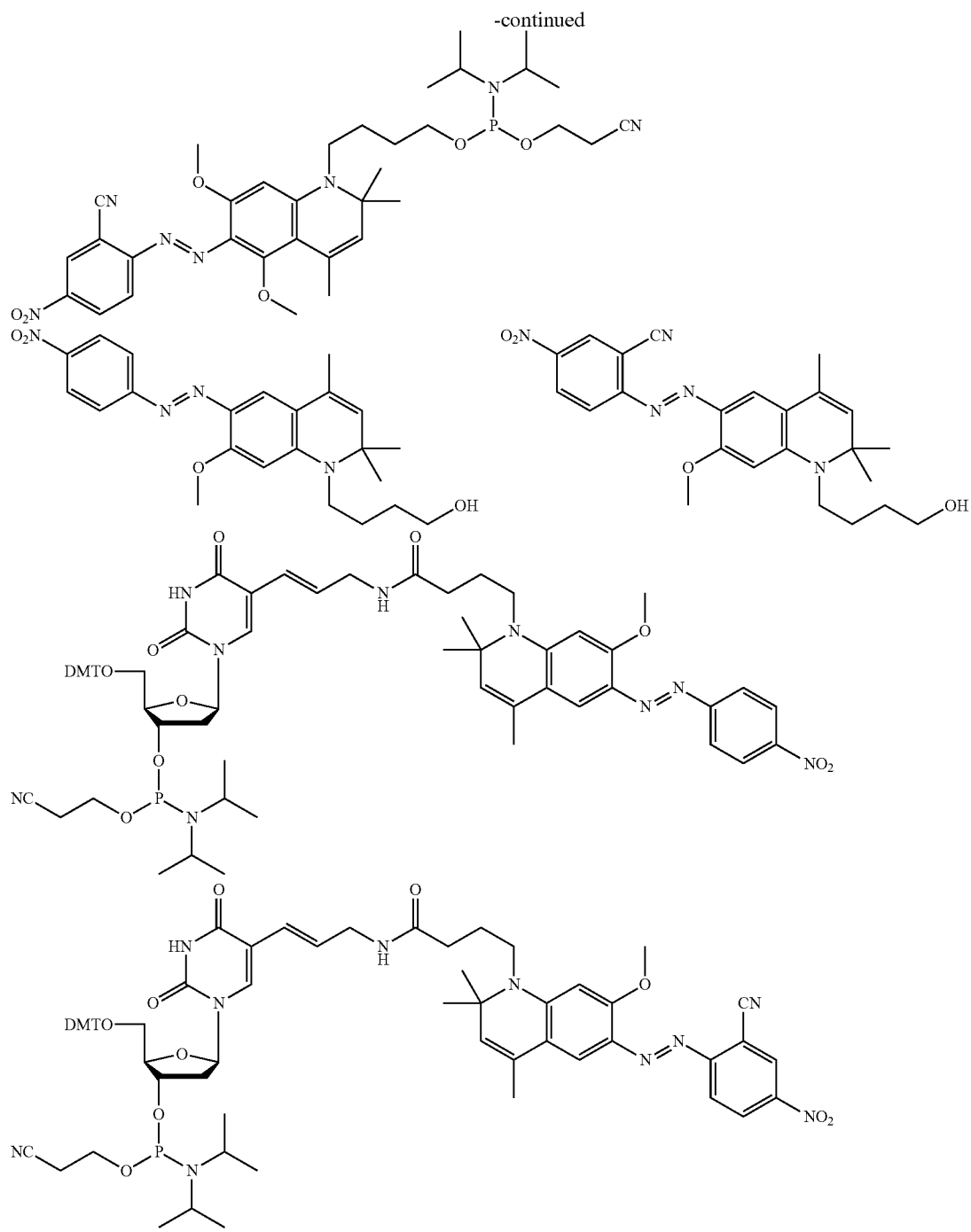

4.3 Methods of Use

In various embodiments, the dyes described herein are attached to a target-specific moiety. In these embodiments, binding between the target-specific moiety and its corresponding target is monitored by essentially determining the presence or amount of dye that is bound to the target. Well-known examples of such assays include hybridizations between complementary nucleic acids as well as binding that take place between antibodies and their corresponding antigens. Other binding pairs of interest include, but are not limited to, ligand/receptor, hormone/hormone receptor, carbohydrate/lectin and enzyme/substrate pairs. In certain embodiments, assays are carried out in which a first component of the binding pair is fixed to a solid support, and a second component of the binding pair is in solution. Accordingly, in these embodiments, by binding to the first component fixed to the support, the second component also is attached to the support. In particular embodiments, the binding pairs described herein are used in microarray assays, where labeled analytes become bound to discrete sites on the microarray. In other particular embodiments, binding pairs described herein are used in homogeneous probe-dependent assays. Examples of such methods include, but are not limited to, energy transfer between adjacent probes (U.S. Pat. No. 4,868,103), the Taqman exonuclease assay (U.S. Pat. Nos. 5,538,848 and 5,210,015), molecular beacon assays (U.S. Pat. Nos. 5,118,801 and 5,925,517) and various real time assays (U.S. patent application Ser. No. 10/096, 076).

In various embodiments, the dyes described herein can be used as quenchers in energy transfer systems for detection and/or quantification of proteins or nucleic acids. In particular embodiments, energy transfer is detected by an increase in signal from a Fluorescence Resonance Energy Transfer (FRET) acceptor as it absorbs energy from a FRET donor. In other systems, energy transfer can be detected by a loss of signal from a donor as it transfers energy to an energy acceptor. See, e.g., Livak et al. (1995) PCR Methods and Applications 4:357-362 (early versions of TaqMan® using Fluorescein as a donor and TAMRA as an acceptor at opposite ends of a probe provided a quenched probe system useful for detecting PCR product); Gibson et al. (1996) Genome Research 6; 995-1001; Wittwer et al. (1997) Biotechniques 22:130-138 (describing TaqMan® or molecular beacon probe assays in which the loss of energy transfer generates a signal or signal is generated by the creation of FRET).

In certain embodiments, the compositions disclosed herein can be used in real-time PCR reactions that utilize a variety of different conformations. See, e.g., Arya et al. (2005) Expert Rev Mol Diagn. 5:209-219; Marras et al. (2005) Clinica Chemica Acta 363:48-60; Wong and Medrano (2005) Biotechniques 39:75-85; and U.S. Pat. No. 8,241,179 (real-time PCR technique in which each primer used for PCR-based amplification has an energy transfer element, and primer locations are designed such that an amplicon has two energy transfer elements in sufficient proximity that energy is transferred from one extended primer to the energy transfer acceptor on the primer of the other strand). Another example of a real-time PCR methods in which the quenchers described herein can be used are described in U.S. Pat. No. 8,241,179 "Process for Quantitative or Qualitative Detection of Single-stranded Nucleic Acids". In this system, multiplex amplification can be carried out using a variety of different fluors where the least complexity is obtained by using either multiple acceptors and a single donor or a single acceptor (such as a quencher described herein) and multiple donors.

In other embodiments, the dyes described herein can be used in methods other than classical PCR methods, such as isothermal amplification systems that generate nucleic acid products and use primers and/or probes labeled with quenchers. See, e.g., Gill and Ghaemi (2008) Nucleosides, Nucleotides and Nucleic Acids 27:224-243. In particular embodiments, the quencher dyes described herein are adapted for use in various immunoassay formats for protein quantification. See, e.g., Niemeyer et al. (2005) TRENDS in Biotechnology 23:208-216, and Gullberg et al. (2004) Proc. Nat Acad Sci (USA) 101:8420-8424.

In a particular embodiment, the dark quencher dyes described herein can be used in methods for detecting qualitatively or quantitatively the presence of a single-stranded nucleic acid of interest in a sample comprising the steps of (a) providing (i) a composition of matter comprising at least two parts: a first part comprising at least one first nucleic acid primer that comprises (A) at least one first energy transfer element; and (B) a nucleic acid sequence that is complementary to a nucleotide sequence in at least a portion of the nucleic acid of interest; and a second part comprising at least one second nucleic acid primer that comprises: (A') at least one second energy transfer element; and (B') a nucleic acid sequence that is identical to a nucleotide sequence in at least a portion of the nucleic acid of interest; wherein the first nucleic acid primer does not comprise the second energy transfer element, and wherein the second nucleic acid primer does not comprise the first energy transfer element, the first energy transfer element is an energy transfer donor and the second energy transfer element is a quencher, or the first energy transfer element is an quencher and the second energy transfer element is an energy transfer donor, and neither the first nucleic acid primer nor the second nucleic acid primer is fixed or immobilized to a solid support; (ii) a sample suspected of containing the nucleic acid of interest; and (iii) reagents for carrying out nucleic acid strand extension; (b) forming a reaction mixture comprising (i), (ii) and (iii) above; (c) contacting under hybridization conditions the first nucleic acid primer with one strand of the nucleic acid of interest and contacting under hybridization conditions the second nucleic acid primer with the complementary strand of the nucleic acid of interest, if present; (d) extending the first nucleic acid primer and the second nucleic acid primer to form a first primer-extended nucleic acid sequence and a second primer-extended nucleic acid sequence if the complementary strand is present; (e) separating the first primer-extended nucleic acid sequence from the nucleic acid of interest and separating the second primer-extended nucleic acid sequence from the complementary strand of the nucleic acid of interest if present; (f) contacting under hybridization conditions the first nucleic acid primer with the nucleic acid of interest or the second primer-extended nucleic acid sequence from step (e), and contacting under hybridization conditions the second nucleic acid primer with the first primer-extended nucleic acid sequence from step (e); and (g) detecting the presence or quantity of the nucleic acid of interest by detecting energy transfer between the first and second energy transfer elements by means of loss of signal from the first energy transfer donors.

5. EXAMPLES

This section will describe the various different working examples that will be used to highlight the features of the invention(s).

5.1 Example 1. Synthesis of 7-methoxy-2,2,4-trimethyl-1, 2-dihydroquinoline (Compound 1)

m-Anisidine (26 ml, 0.23 mol) was added slowly to acetic acid (2.6 ml) with stirring, followed by the addition of mesityl oxide (27 ml, 0.23 mol) to the solution. The mixture was stirred at room temperature overnight. Concentrated hydrobromic acid (50 ml) was added. The mixture was stirred for an additional hour. The solid formed was collected by filtration and then washed with acetone (3×50 mL). The resulting solid was dissolved in water (100 ml) and neutralized to pH 7 with 10N aqueous sodium hydroxide. The precipitate was extracted with chloroform (3×50 mL) and dry over anhydrous sodium sulfate. After filtering off sodium sulfate, the solvent was evaporated under vacuum to give crude product. The crude product was recrystallized with hexanes to give compound 1 as yellowish solid (15.5 g, 33% yield). The structure of compound 1 is given below:

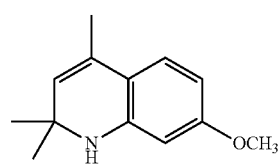

1

5.2 Example 2. Synthesis of 4-(7-methoxy-2,2,4-trimethylquinolin-1(2H)-yl)butanoic acid (Compound 3)

Calcium carbonate (6.01 g, 60 mmols) and ethyl 4-bromobutyrate (9.75 g, 50 mmols) were added to a solution of compound 1 7-methoxy-2,2,4-trimethyl-1,2-dihydroquinoline (8.12 g, 40 mmols) in anhydrous DMF (100 ml). The mixture was stirred at 120° C. for 3 days (reaction was monitored by TLC: hexane/ethyl acetate, 4/1). The solvent was removed under vacuum. The residue was redissolved in ethyl acetate (200 mL) and filtered through celite. The solvent was removed under vacuum to give crude ester 2.

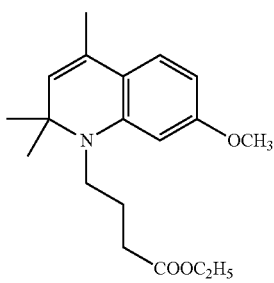

2

The crude ester 2 was dissolved in methanol (150 mL) and water (20 mL). Potassium hydroxide (6 g) was added. The mixture was stirred at room temperature for one day. The solvent was removed under vacuum. Water (200 mL) and ethyl ether (150 mL) were added to the residue. The water layer was extracted with ethyl ether (2×150 mL) and then neutralized to pH 3-4 with 6N HCl. The mixture was extracted with ethyl acetate (3×150 mL). The combined ethyl acetate layer was washed with water (2×150 mL) and brine (200 mL) and then dried with anhydrous sodium sulfate. The solvent was removed under vacuum to give compound 3 as viscous oil (6.7 g, 58%). The structure of compound 3 is given below:

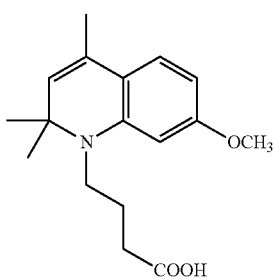

3

5.3 Example 3. Synthesis of 4-nitrobenzenediazonium tetrafluoroborate (Compound 4)

A suspension of 4-nitroaniline (6.216 g, 45 mmols) in 4N HCl (50 mL) was stirred and cooled with an ice bath for 15 min. A solution of sodium nitrite (3.42 g, 49.5 mmols) in water (20 mL) was added slowly. After the addition, the mixture was stirred at this temperature for 30 min. A solution of lithium tetrafluoroborate (5.9 g, 63 mmols) in water (20 mL) was added. The solid precipitate was collected by filtration and washed with water (2×25 mL), methanol (25 mL) and ether (2×25 mL). The precipitate was dried under vacuum overnight to give compound 4 as off-white solid (7.518 g, 71%). The structure of compound 4 is given below:

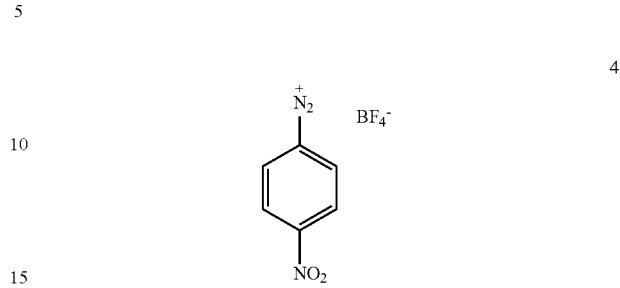

4

5.4 Example 4. Synthesis of (E)-4-(7-methoxy-2,2,4-trimethyl-6-((4-nitrophenyl)diazenyl)quinolin-1(2H)-yl)butanoic acid (Compound 5)

Compound 4 (2.39 g, 10.1 mmols) was added in small batches to a solution of compound 3 (2.43 g, 8.40 mmols) in pyridine (50 mL) at room temperature with stirring. The mixture was stirred at room temperature for 3 hours (monitor the reaction by TLC: 5% methanol in dichloromethane). The solvent was removed under vacuum. The residue was redissolved in dichloromethane (200 mL) and water (200 mL). The dichloromethane layer was washed with water (3×200 mL) and dried with anhydrous sodium sulfate. The solvent was removed under vacuum. The residue was purified by flash chromatography (gradient: 0-5% methanol in dichloromethane) to afford compound 5 as dark solid (1.70 g, 46%). The structure of compound 5 is given below:

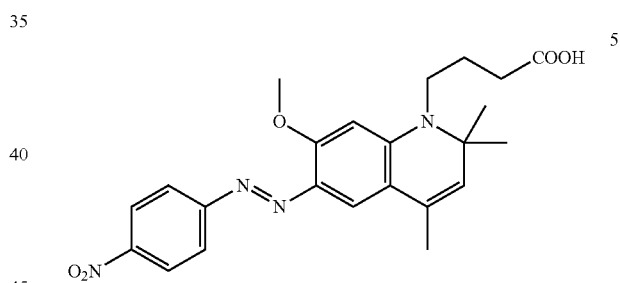

5

5.5 Example 5. Synthesis of (E)-2,5-dioxopyrrolidin-1-yl 4-(7-methoxy-2,2,4-trimethyl-6-((4-nitrophenyl)diazenyl)quinolin-1(2H)-yl)butanoate (Compound 6)

Method 1: In Situ Activation

A 20 mM solution of compound 5 in DMF (50 µl) was mixed with a 100 mM solution of TSTU (2-succinimido-1,1,3,3-tetramethyluronium tetrafluoroborate) in DMF (11 µl, 1.1 equivalent) and a 300 mM solution of DIPEA (diisopropylethylamine) in DMF (7.3 µl, 2.2 equivalent). The mixture was kept at room temperature for 1 hour (monitor the reaction with TLC: hexanes/ethyl acetate, 2/1). The solution was used directly for conjugation with biomolecules.

Method 2: Synthesis of Compound 6 (Isolated)

TSTU (2-succinimido-1,1,3,3-tetramethyluronium tetrafluoroborate, 412 mg, 1.37 mmols) and DIPEA (diisopropylethylamine, 390.3 µL, 2.28 mmols) was added to a solution of compound 5 (500 mg, 1.14 mmols) in DMF (20 mL). The mixture was stirred at room temperature for 3 hours (monitor the reaction by TLC: hexanes/ethyl acetate, 2/1). The solvent was evaporated to dryness under vacuum.

The residue was dissolved in dichloromethane (200 mL) and washed with water (3×200 mL) and brine (200 mL). The solution was dried with anhydrous sodium sulfate, then filtered and evaporated to dryness to give product as a dark solid (136.5 mg, 22%). The structure of compound 6 is given below:

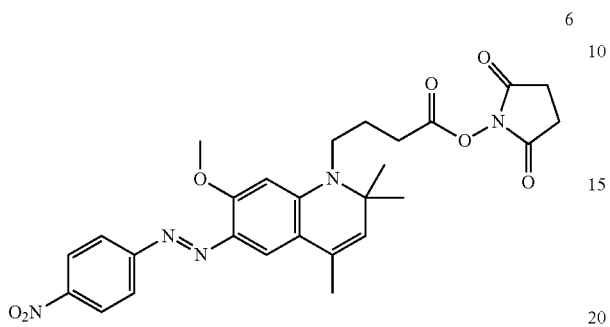

5.6 Example 6. Synthesis of 4-(7-methoxy-2,2,4-trimethyl-3,4-dihydroquinolin-1(2H)-yl)butanoic acid (Compound 7)

Palladium on carbon (10% w/w, 0.1 g) was added to a solution of compound 3 (0.9 g) in methanol (50 mL). The mixture was shaken on a hydrogenation apparatus under 50 psi of hydrogen. After the reaction was complete (as monitored by TLC: hexanes/ethyl acetate, 4/1), the mixture was filtered through a pad of celite. The solvent was removed under vacuum to provide compound 7 as a dark green solid (0.8 g, 88%). The structure of compound 7 is given below:

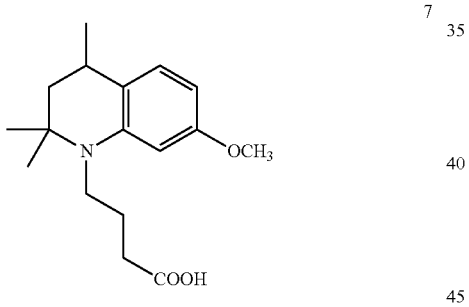

5.7 Example 7. Synthesis of (E)-4-(7-methoxy-2,2,4-trimethyl-6-((4-nitrophenyl)diazenyl)-3,4-dihydroquinolin-1(2H)-yl)butanoic acid (Compound 8)

Compound 8 (25.5 mg, 58%) was made from compound 7 (29.1 mg) and compound 4 (23.7 mg) following the procedure in Example 4. The structure of compound 8 is given below:

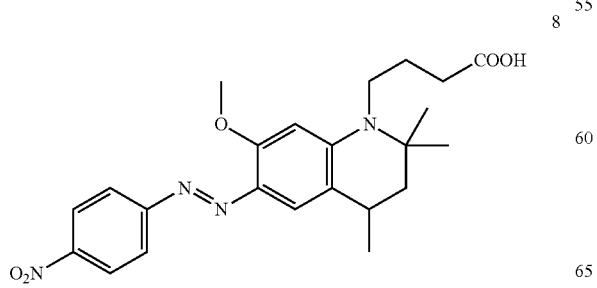

5.8 Example 8. Synthesis of (E)-2,5-dioxopyrrolidin-1-yl 4-(7-methoxy-2,2,4-trimethyl-6-((4-nitrophenyl)diazenyl)-3,4-dihydroquinolin-1(2H)-yl)butanoate (Compound 9)

Compound 9 was made from compound 8 following the procedure in Example 5. The structure of compound 9 is given below given below:

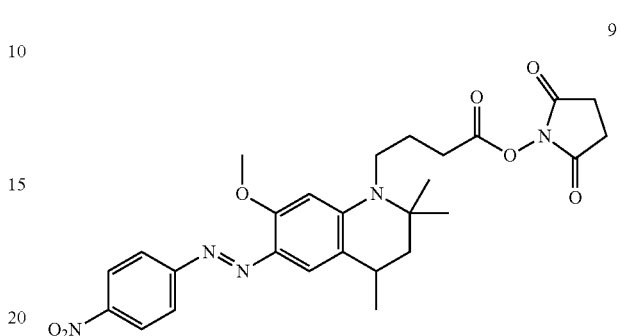

5.9 Example 9. Synthesis of (E)-4-(7-methoxy-6-((2-methoxy-4-nitrophenyl)diazenyl)-2,2,4-trimethyl-3,4-dihydroquinolin-1(2H)-yl)butanoic acid (Compound 10)

Compound 10 (98.2 mg, 36%) was made from compound 7 (171 mg) and Fast Red B salt (274.3 mg) following the procedure in Example 4. The structure of Compound 10 is given below:

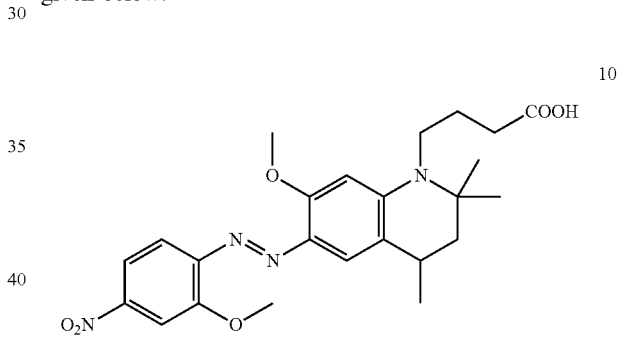

5.10 Example 10. Synthesis of (E)-2,5-dioxopyrrolidin-1-yl 4-(7-methoxy-6-((2-methoxy-4-nitrophenyl)diazenyl)-2,2,4-trimethyl-3,4-dihydroquinolin-1(2H)-yl)butanoate (Compound 11)

Compound 11 was made from compound 10 following the procedure in Example 5. The structure of compound 11 is given below:

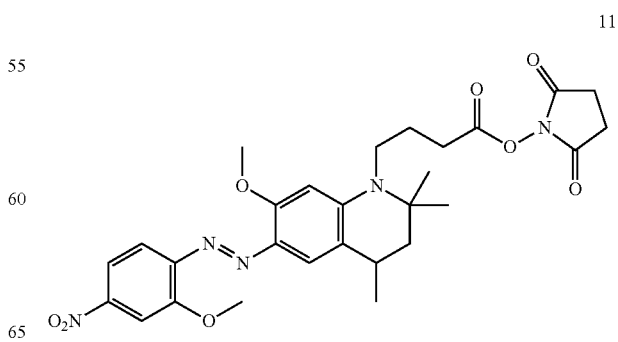

5.11 Example 11. Synthesis of 2-chloro-4-nitrobenzenediazonium tetrafluoroborate (Compound 12)

Compound 12 (1.52 g, 12%) was prepared from 2-chloro-4-nitroaniline (7.77 g) following the procedure in Example 3. The structure of Compound 12 is given below:

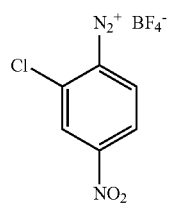

12

5.12 Example 12. Synthesis of (E)-4-(6-((2-chloro-4-nitrophenyl)diazenyl)-7-methoxy-2,2,4-trimethylquinolin-1(2H)-yl)butanoic acid (Compound 13)

Compound 13 (7.2 mg, 15%) was prepared from compound 12 (27.1 mg) and compound 3 (28.9 mg) following the procedure in Example 4. The structure of Compound 13 is given below:

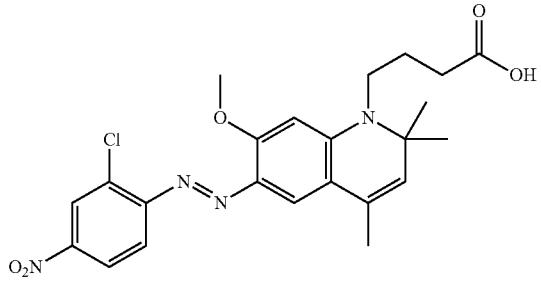

13

5.13 Example 13. Synthesis of (E)-2,5-dioxopyrrolidin-1-yl 4-(6-((2-chloro-4-nitrophenyl)diazenyl)-7-methoxy-2,2,4-trimethylquinolin-1(2H)-yl)butanoate (Compound 14)

Compound 14 was prepared from compound 13 following the procedure in Example 5. The structure of Compound 14 is given below:

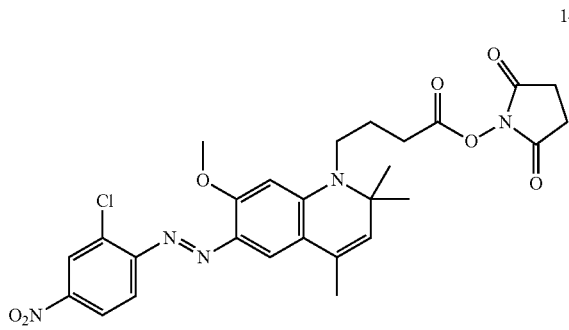

14

5.14 Example 14. Synthesis of (E)-4-(7-methoxy-2,2,4-trimethyl-6-((5-nitrothiazol-2-yl)diazenyl)-3,4-dihydroquinolin-1(2H)-yl)butanoic acid (Compound 15)

Sodium nitrite (58.1 mg) was added slowly to concentrated sulfuric acid (0.42 mL) with shaking and cooling. The mixture was maintained at 0° C. for 30 min, then added to a solution of 2-amino-5-nitrobenzothiazole (120 mg) in acetic acid (1.5 mL) at room temperature. After the resulting mixture was stirred at 0° C. for 1 hour, a solution of compound 7 (200 mg) in acetic acid (1.9 mL) was added. The mixture was stirred at room temperature for 3 hours, and then poured into ice-water (15 mL). The resultant precipitate was extracted with ethyl acetate (3×15 mL) and the combined ethyl acetate layer was washed with water (3×30 mL) and brine (30 mL). After drying with anhydrous sodium sulfate, the solvent was removed under vacuum. The residue was purified by flash chromatography (gradient: 0% to 5% of methanol in dichloromethane) to give compound 15 as dark solid (40.1 mg, 11%). The structure of compound 15 is given below:

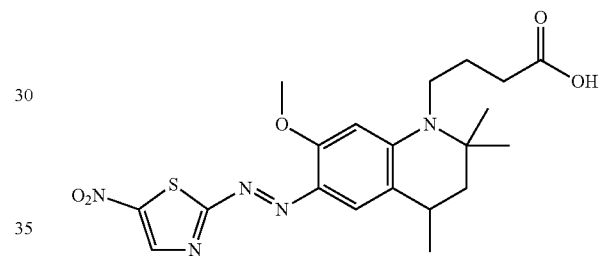

15

5.15 Example 15. Synthesis of (E)-2,5-dioxopyrrolidin-1-yl 4-(7-methoxy-2,2,4-trimethyl-6-((5-nitrothiazol-2-yl)diazenyl)-3,4-dihydroquinolin-1(2H)-yl)butanoate (Compound 16)

Compound 16 was prepared from compound 15 following the procedure as in Example 5. The structure of compound 16 is given below:

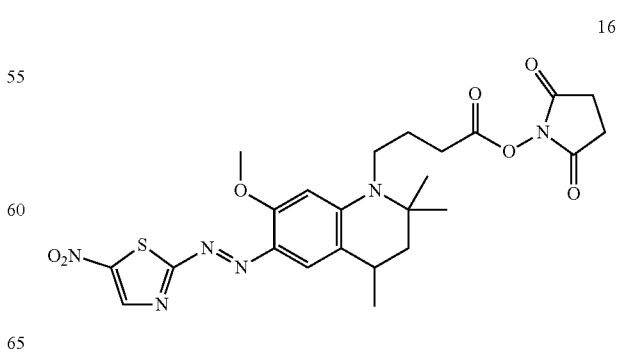

16

5.16 Example 16. Synthesis of (E)-4-(7-methoxy-2,2,4-trimethyl-6-((5-nitrothiazol-2-yl)diazenyl)quinolin-1(2H)-yl)butanoic acid (Compound 17)

Compound 17 (20.3 mg, 23%) was prepared from compound 3 (57.9 mg) following the procedure as in Example 14. The structure of compound 17 is given below:

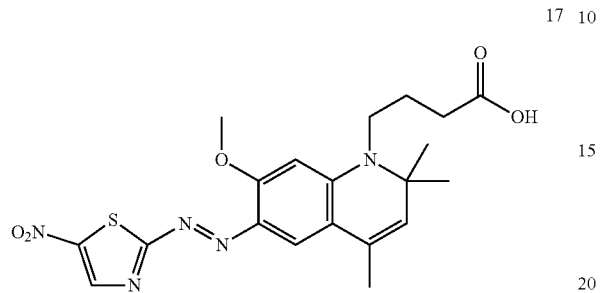

5.17 Example 17. Synthesis of (E)-2,5-dioxopyrrolidin-1-yl 4-(7-methoxy-2,2,4-trimethyl-6-((5-nitrothiazol-2-yl)diazenyl)quinolin-1(2H)-yl)butanoate (Compound 18)

Compound 18 was prepared from compound 17 following the procedure as in Example 5. The structure of compound 18 is given below:

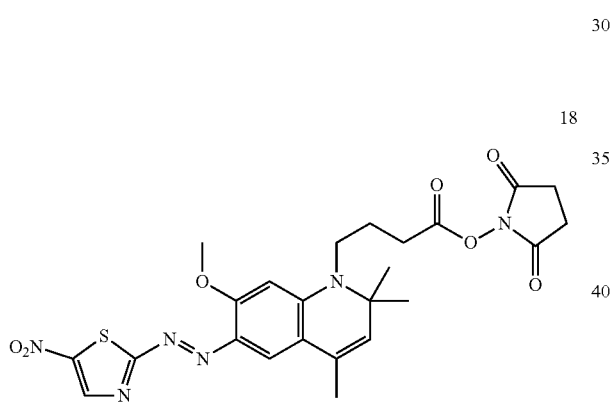

5.18 Example 18. Synthesis of 5,7-dimethoxy-2,2,4-trimethyl-1,2-dihydroquinoline (Compound 19)

Compound 19 (19.3 g, 83%) was prepared from 3,5-dimethoxyaniline (15.3 mg) following the procedure in Example 1. The structure of compound 19 is given below:

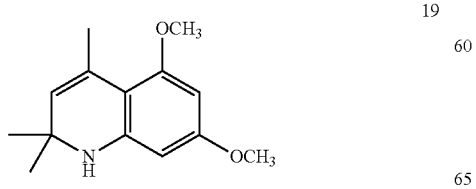

5.19 Example 19. Synthesis of 5,7-dimethoxy-2,2,4-trimethyl-1,2-dihydroquinoline (Compound 21)

Compound 21 (11.2g, 70%) was prepared through compound 20 from compound 19 (11.67 g) following the procedure as in Example 2. The structures of compound 20 and compound 21 are given below:

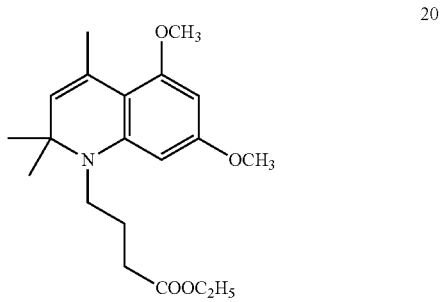

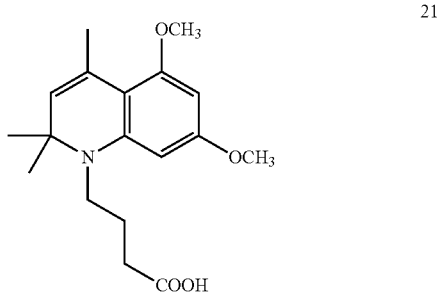

5.20 Example 20. Synthesis of (E)-4-(6-((2-cyano-4-nitrophenyl)diazenyl)-7-methoxy-2,2,4-trimethylquinolin-1(2H)-yl)butanoic acid (Compound 22)

Compound 22 (265.3mg, 33%) was prepared from 2-amino-5-nitrobenzonitrile (338 mg) and compound 3 (500 mg) following the procedure as in Example 14. The structure of compound 22 is given below:

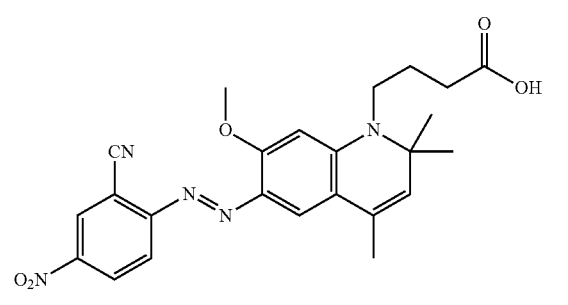

5.21 Example 21. Synthesis of (E)-2,5-dioxopyrrolidin-1-yl 4-(6-((2-cyano-4-nitrophenyl)diazenyl)-7-methoxy-2,2,4-trimethylquinolin-1(2H)-yl)butanoate (Compound 23)

Compound 23 was prepared from compound 22 following the procedure as in Example 5. The structure of compound 23 is given below:

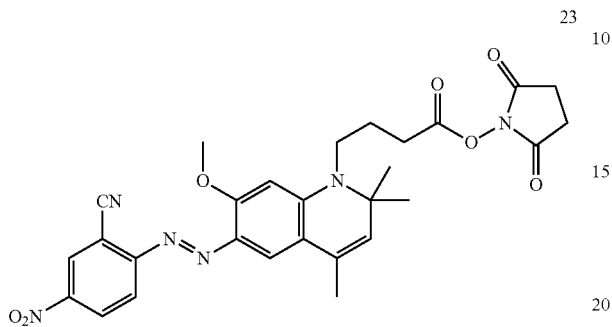

23

5.22 Example 22. Synthesis of (E)-4-(6-((2-cyano-4-nitrophenyl)diazenyl)-5,7-dimethoxy-2,2,4-trimethylquinolin-1(2H)-yl)butanoic acid (Compound 24)

Compound 24 (22.1 mg, 22%) was prepared from compound 21 (63.9 mg) and 2-amino-5-nitrobenzonitrile (32.5 mg) following the procedure in Example 14. The structure of compound 24 is given below:

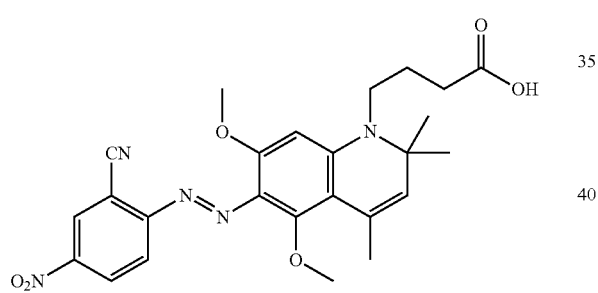

24

5.23 Example 23. Synthesis of (E)-2,5-dioxopyrrolidin-1-yl 4-(6-((2-cyano-4-nitrophenyl)diazenyl)-5,7-dimethoxy-2,2,4-trimethylquinolin-1(2H)-yl)butanoate (Compound 25)

Compound 25 was prepared from compound 24 following the procedure in Example 5. The structure of compound 25 is given below:

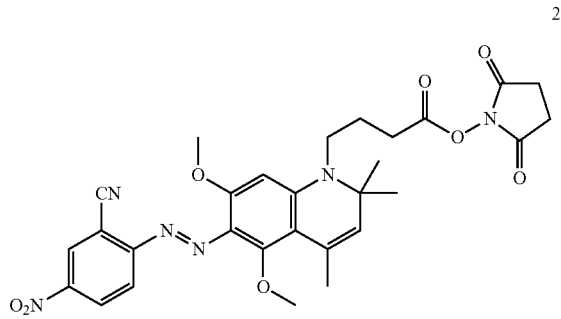 [SMILES: COc1cc2c(cc1/N=N/c1ccc([N+](=O)[O-])cc1C#N)C(C)=CC(C)(C)N2CCCC(=O)ON1C(=O)CCC1=O]

25

5.24 Example 24. Synthesis of Compound 26

Compound 26 was prepared from compound 1 and 4-bromobutanol following the procedure in Example 2. The structure of compound 26 is given below:

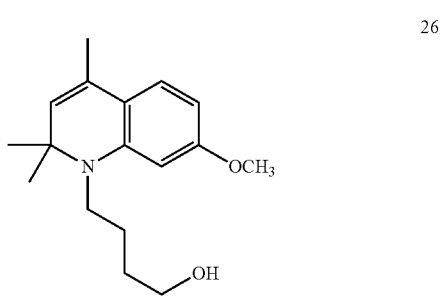 [SMILES: COc1ccc2c(c1)N(CCCCO)C(C)(C)C=C2C]

26

5.25 Example 25. Synthesis of Compound 27

Compound 27 was prepared from compound 4 and compound 26 following the procedure in Example 4. The structure of compound 27 is given below:

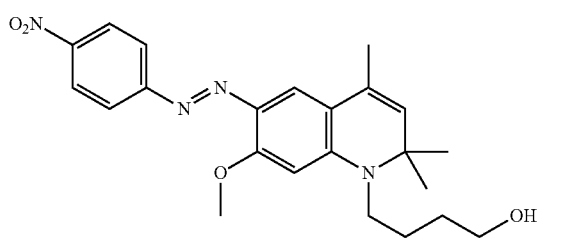

27

5.26 Example 26. Synthesis of Compound 28

A solution of 2-cyanoethyl tetraisopropylphosphorodiamidite (190 mg, 0.64 mmol) in dichloromethane (5 mL) was added to a solution of compound 27 (255 mg, 0.6 mmol) and diisopropylammonium tetrazolide (52 mg, 0.3 mmol) in dichloromethane (10 mL) at room temperature. After the mixture was stirred at room temperature overnight, it was washed with saturated sodium bicarbonate (15 mL), water (2×15 mL) and brine (15 mL). The solution was dried with anhydrous sodium sulfate and then evaporated under vacuum. The resulting crude product was purified by flash chromatography on silica gel. Compound 28 was obtained as a dark colored powder (232 mg, 62%). The structure of compound 28 is given below:

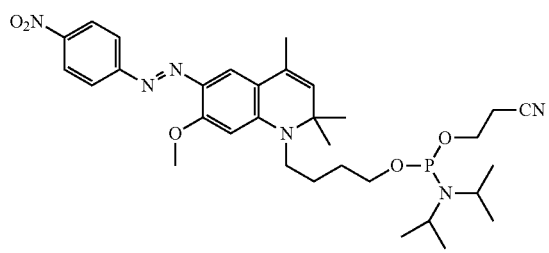

28

5.27 Example 27. Synthesis of Compound 29

Compound 29 was prepared from 2-amino-5-nitrobenzonitrile and compound 26 following the procedure in Example 20. The structure of compound 29 is given below:

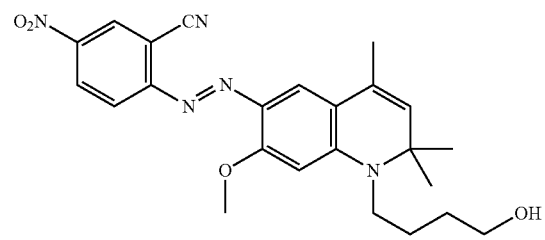

29

5.28 Example 28. Synthesis of Compound 30

Compound 30 was prepared from compound 29 following the procedure in Example 26. The structure of compound 30 is given below:

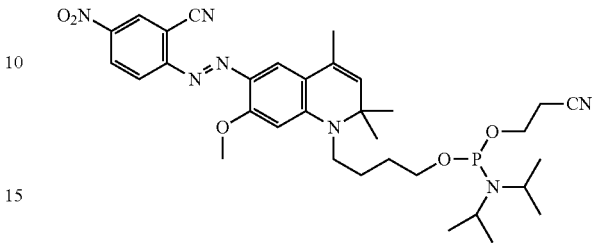

30

5.29 Example 29. Synthesis of Compound 31

To a solution of DMT protected 5-allylamine-dU (Enzo Life Sciences, Inc., 58.6 mg, 0.1 mmol) in acetonitrile (10 mL) was added a solution of compound 6 (53.6 mg, 0.1 mmol) in acetonitrile (5 mL). The mixture was stirred at room temperature overnight and then solvent was evaporated under vacuum. The residue was dissolved in dichloromethane (50 mL). It was washed with water (3×20 mL), brine (40 mL) and then dried with anhydrous sodium sulfate. The solvent was removed under vacuum. The crude product was purified by flash chromatography to provide compound 31 as a dark solid (85.9 mg, 84%). The structure of compound 31 is given below:

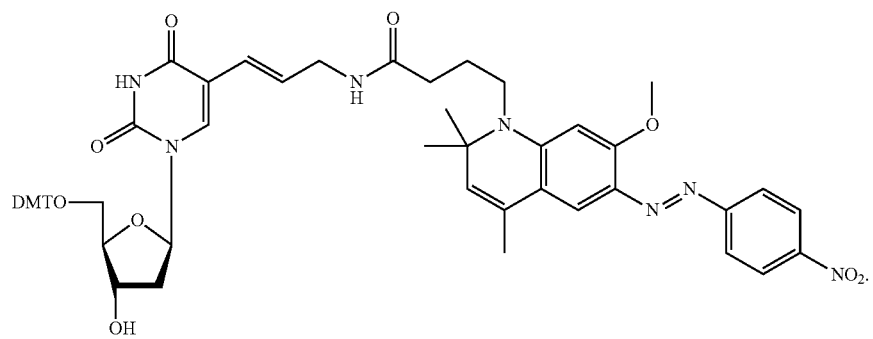

31

5.30 Example 30. Synthesis of Compound 32

Compound 32 was prepared from compound 31 following procedure in Example 26. The structure of compound 32 is given below:

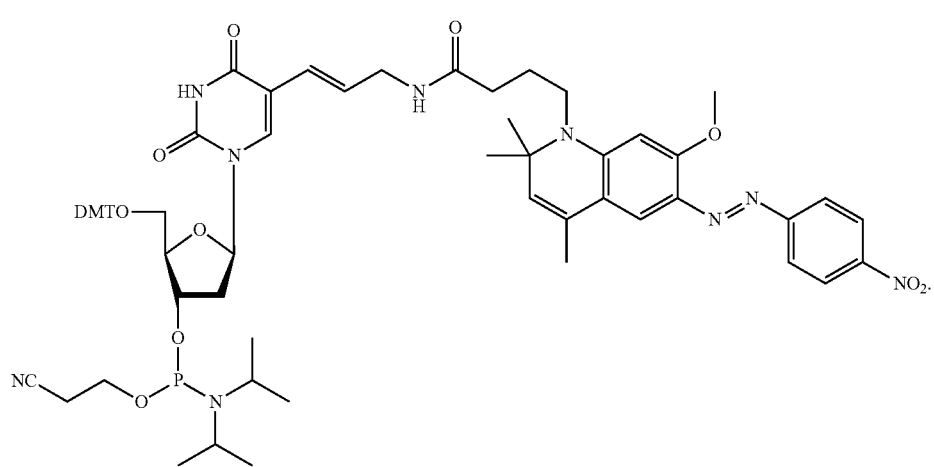

32

5.31 Example 31. Synthesis of Compound 33

Compound 33 was prepared from compound 23 following the procedure in Example 29. The structure of compound 33 is given below:

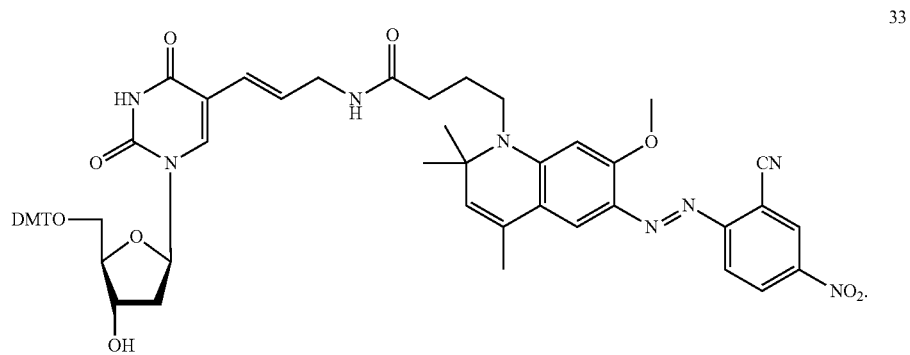

33

5.32 Example 32. Synthesis of Compound 34

Compound 34 was prepared from compound 33 following the procedure in Example 26. The structure of compound 34 is given below:

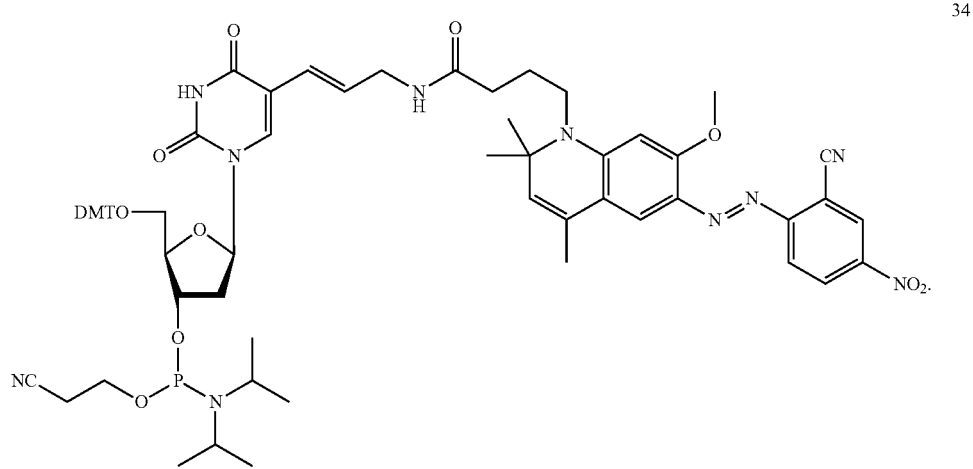

34

5.33 Example 33. General Procedure for Conjugation to Oligonucleotide (with Compound 5 as an Example)

Compound 5 (2 µmol) was dissolved in amine-free DMF (140 µl), followed by the addition of 2-succinimido-1,1,3,3-tetramethyluronium tetrafluoroborate (2.4 µmols) and diisopropylethylamine (4.4 µmols). The mixture was stirred at room temperature for 30 min, and then added to a solution of oligonucleotide containing an amine linker (80 nmols) in 0.9 M sodium borate buffer (320 µL, pH 8.5). The combined mixture was stirred at room temperature for 16 h. Solvents were removed under vacuum and the residue pellet was purified by HPLC using a gradient of triethylammoniumacetate (0.1 M, pH 6.9) and acetonitrile as eluting solvents. The fractions containing pure conjugates were combined, evaporated, and co-evaporated with water to remove excessive salt. The final blue pellet was dissolved in water and stored at −20° C. until further use.

5.34 Example 34. General Procedure of Conjugation with Streptavidin (with Compound 5 as an Example)

Compound 5 (175 nmol) was dissolved in amine-free DMF (35 µl), followed by the addition of 2-succinimido-1,1,3,3-tetramethyluronium tetrafluoroborate (192.5 nmol) and diisopropylethylamine (350 nmol). The mixture was stirred at room temperature for 60 min, and then added in small aliquots to a solution of streptavidin (17.5 nmol) in 100 mM carbonate/bicarbonate buffer (350 µL). The mixture was stirred at room temperature for 1 hour. The mixture was loaded to the top of a NAP™ 25 gel filtration column and eluted with 1×PBS buffer. The fractions containing the dye-streptavidin conjugate were combined. BSA solution (50 mM, 43.2 µL) and 20% $NaN_3$ solution (7.5 µL) were added. The mixture was stored at 4° C.

5.35 Example 35. General Procedure of Conjugation to Amine Modified Nucleotides Using Compound 5 as an Example Compound 5 (12 µmol) was dissolved in amine-free DMF (840 µl), followed by the addition of 2-succinimido-1,1,3,3-tetramethyluronium tetrafluoroborate (14.4 µmol) and diisopropylethylamine (26.4 µmol). The mixture was stirred at room temperature for 60 min, and then added to a solution of allylamine-dUTP (2'-deoxyuridine, 5'-triphosphate, 10 µmol) in 0.1 M sodium borate buffer (840 µL, pH 8.5). The mixture was stirred at room temperature for 16 h. Pure product (3.8 µmol, 38% yield) was obtained by ion exchange chromatography. The structure of the allylamine-dUTP and compound 5 conjugate is given below:

The conjugates of compound 5 with ATP, GTP, CTP, TTP, UTP, dATP, dGTP, dCTP, dTTP, ddUTP, ddATP and ddCTP were prepared through similar procedures using respective modified nucleotides containing amino groups.

5.36 Example 36. qPCR Studies with Compound 6 and 23

Compounds 6 and 23 were shown to function in a qPCR assay (Enzo Life Sciences Inc., Farmingdale, N.Y., U.S. Pat. No. 8,247,179). The fluorescent dye labeled oligo YpF574 (5'-CAGACGA-ATTCATTTGCCTGAAGTAG-3') [SEQ ID NO:1] labeled on the third base from the 3' end was used with compound 6 and 23 labeled oligo YpR600 (5'-ATCATGAGTTGAAATCACT-GGTT-CCTC-3') [SEQ ID NO:2] labeled on the penultimate base to amplify the target sequence CAGACGAATTCGATTTGCCTGAAGTAGAG-GAACCAGTGATTTCAACTCATGAAT [SEQ ID NO:3], or an unmatched sequence. The oligos were purchased with an amino group on the 5 position of the thymine base for labeling with various dyes. The NHS ester of the dye (Fluorescein, Red598s or Cy5) or compound 6 and 23 were added in a 20-fold excess to the oligo in 50 mM sodium carbonate, pH 9.6, 50% dimethyl formamide, and incubated with shaking at 22° C. for 2 hours. The reaction mixture was then dried in a SpeedVac vacuum concentrator. The dried oligos were resuspended in 400 µl water and 40 µl of 3 M sodium acetate, pH 5.3 was added to this, followed by 1 ml of ice cold ethanol. The combined mixture was then chilled at −80° C. for 1 hour, and then centrifuged at 16,000×g for 45 minutes. The supernatant containing unincorporated dye was removed using vacuum aspiration. 400 µl of 70% ethanol was added, and the tube was again centrifuged for 30 minutes at 16,000×g. The supernatant was removed using vacuum aspiration. After removal of all ethanol, the oligos were resuspended in 50 µl of water. The oligos were HPLC purified prior to use in PCR using standard methods known to those in the field.

PCR was performed with 0.55 µM of the YpF574 and YpR600 in buffer (50 mM HEPES, pH 7.6, 10 mM KCl, 10 mM $(NH_4)_2SO_4$, 2.5 mM $MgCl_2$, 0.002% Tween20, 5% sucrose, 200 mM Betaine, 160 mM 1,2-propanediol, 200 mM each of the dNTPs) with 1.5 units of Ampigene HS Taq DNA Polymerase (ENZO, Farmingdale, N.Y.). About 10 to 20 copies of the target DNA mixed with 1 µg/ml single-stranded Salmon Sperm DNA (SIGMA, St. Louis, Mo.) and then added to the reaction, and the enzyme was activated at 95° C. for 5 minutes followed by 55 cycles of 95° C. 15 seconds, 68° 40 seconds. Fluorescence measurement was

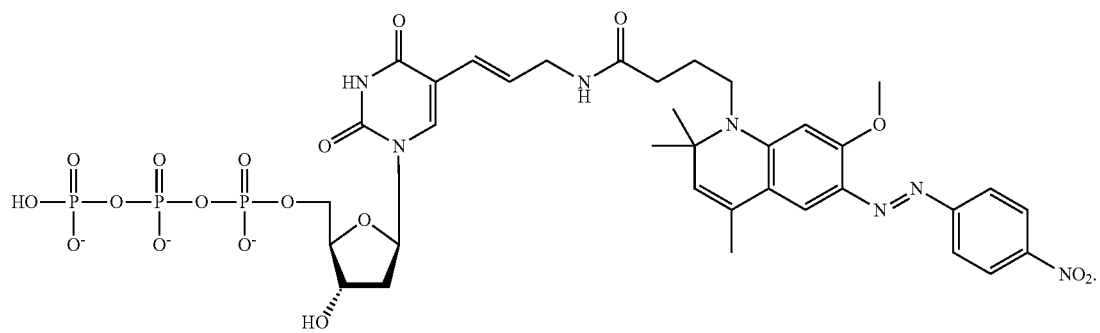

35 recorded after the 68° step. The reaction was performed in either a Qiagen Rotorgene (for Cy5) or Roche LightCycler 2 (for Fluorescein and ENZO Red598). FIGS. 7-9 show the quenching functionality of compounds 6 and 23 with various dyes.

5.37 Example 37. Analysis of High Risk HPV+ Patient Pap Smears for E6/E7 Viral mRNA Using Compound 6

A molecular beacon with a hairpin structure with 6-FAM on the 5' end and compound 6 on the 3' end was used in this study. This construct was targeted to the mRNA of high risk HPV E6/E7 (each probe at a concentration of 8 nM).

Pap smear samples fixed in ThinPrep solution were spun down, supernatant was aspirated, and cells were resuspended in PBS containing 5% formaldehyde. Cells were incubated for 30 minutes, then washed 3 times with PBS. Cells were resuspended in hybridization buffer (2% Triton X-100 in 1×SSC) containing a cocktail of molecular beacons. Cells were incubated in the dark at 65° C. for 1 hour to induce hybridization to the target sequences, then at 4° C. for 30 minutes to ensure unbound probes returned to their hairpin structure. Cells were then run in a FACSCalibur flow cytometer to measure bound beacons. FIG. 10 shows a typical E6/E7 negative Pap smear sample and FIG. 11 a typical E6/E7 positive Pap smear sample.

What is claimed is:
1. A compound selected from the group consisting of
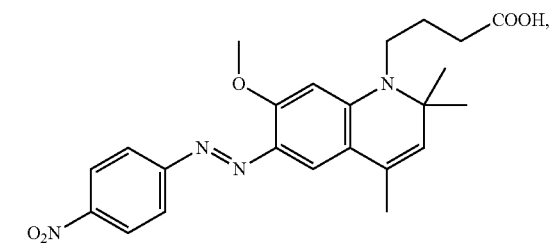
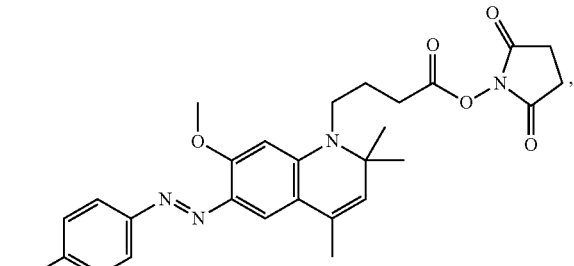
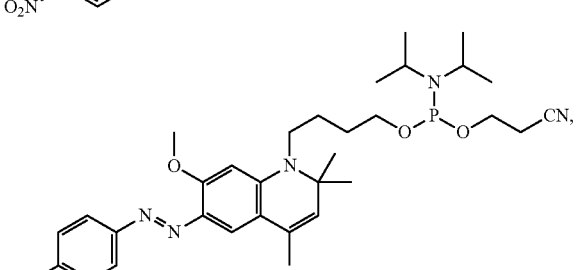
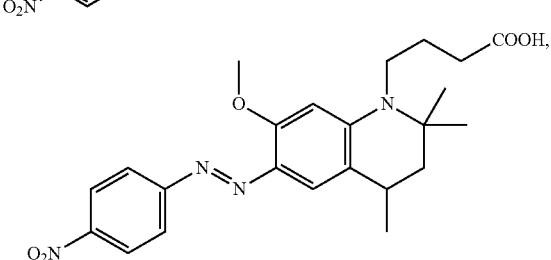
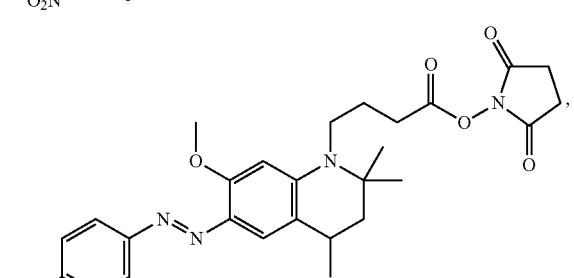
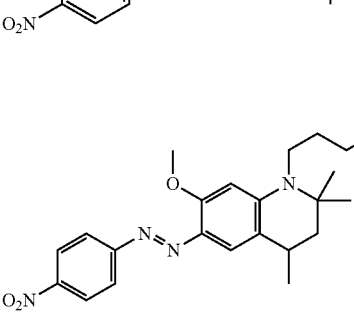
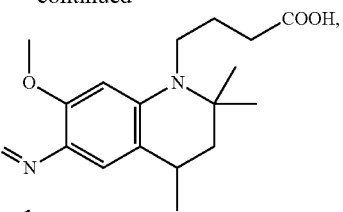
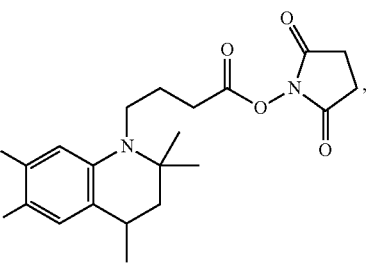
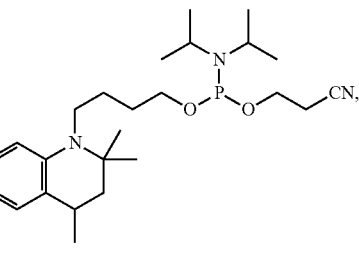
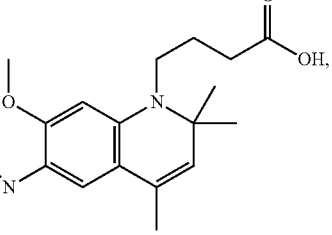
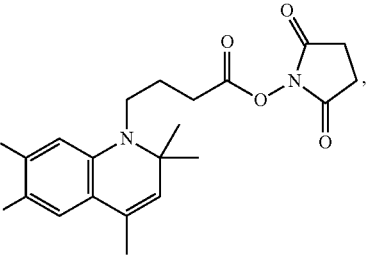
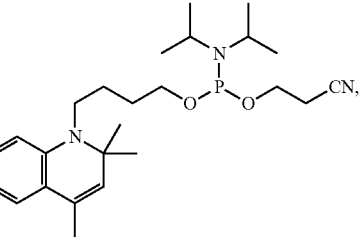

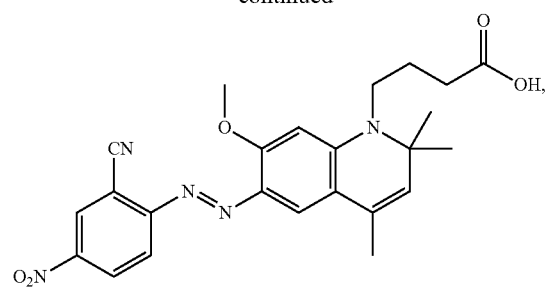
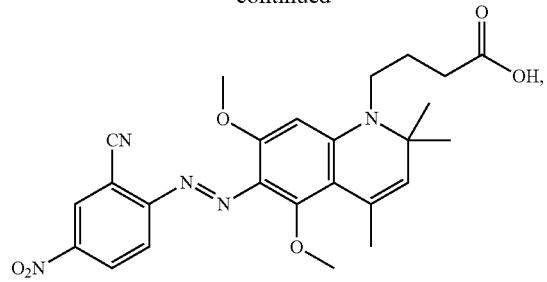
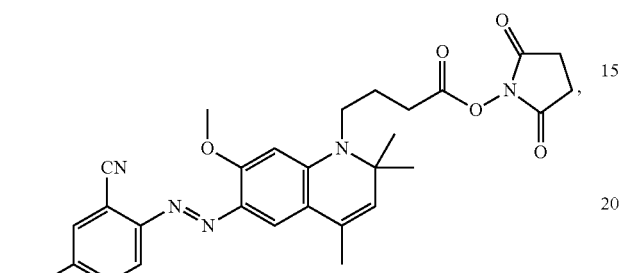
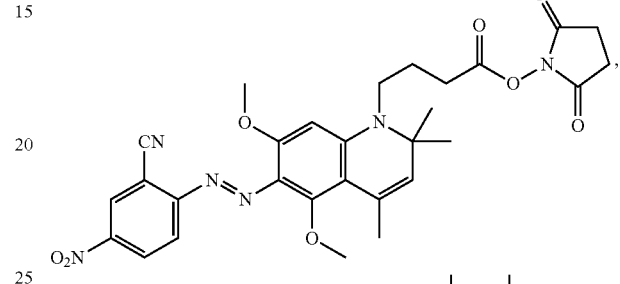
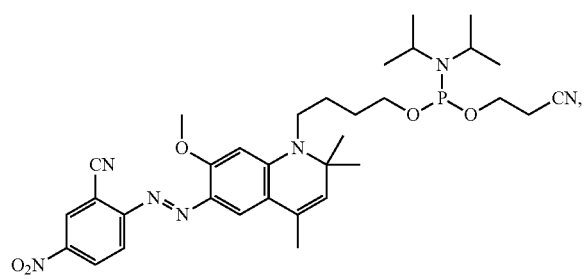
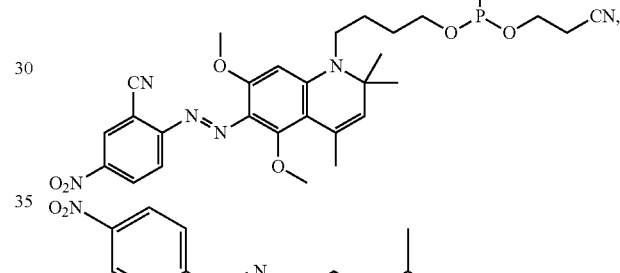
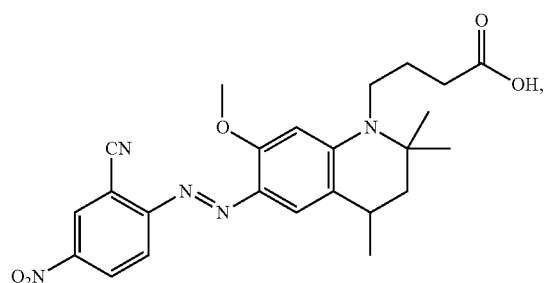
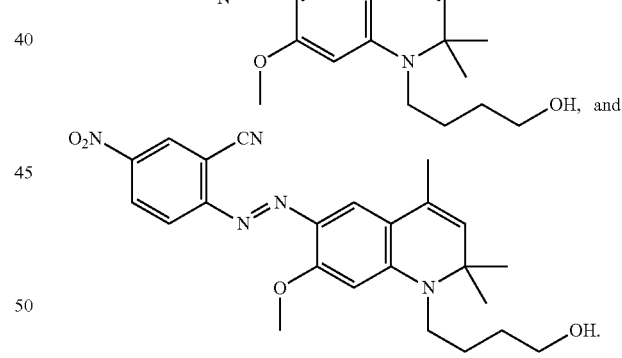
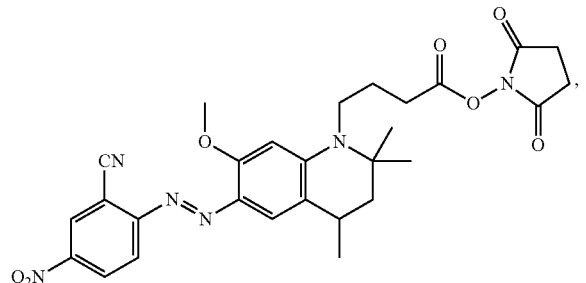
2. The compound of claim 1 having the structure
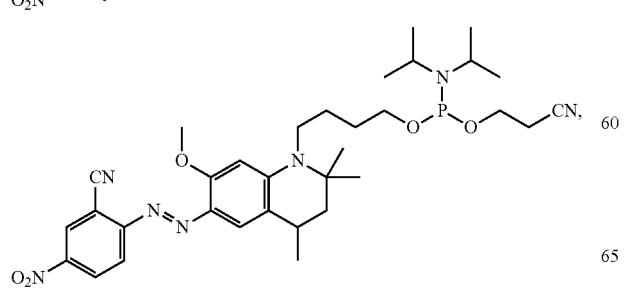
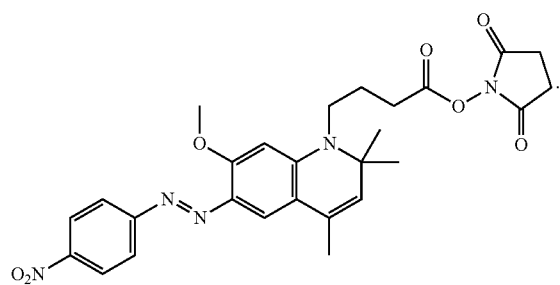 [SMILES: COc1cc2c(cc1/N=N/c1ccc([N+](=O)[O-])cc1)C(C)=CC(C)(C)N2CCCC(=O)ON1C(=O)CCC1=O ; "."]

3. The compound of claim 1 having the structure
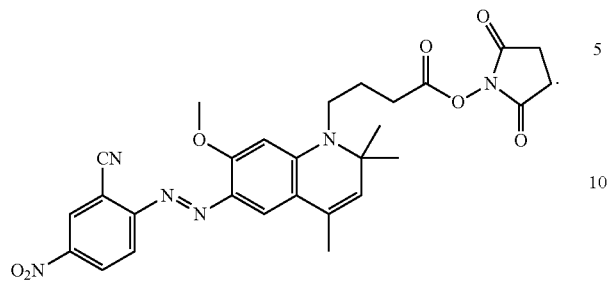
* * * * *

```
                        SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 1
cagacgaatt catttgcctg aagtag                                         26

<210> SEQ ID NO 2
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 2
attcatgagt tgaaatcact ggttcctc                                       28

<210> SEQ ID NO 3
<211> LENGTH: 54
<212> TYPE: DNA
<213> ORGANISM: Unknown
<220> FEATURE:
<223> OTHER INFORMATION: TARGET SEQUENCE

<400> SEQUENCE: 3
cagacgaatt cgatttgcct gaagtagagg aaccagtgat ttcaactcat gaat          54
```